United States Patent [19]
Hunter et al.

[11] Patent Number: 5,835,205
[45] Date of Patent: Nov. 10, 1998

[54] OPTICAL TESTING SYSTEM FOR DISTINGUISHING A SILICON CARBIDE GEMSTONE FROM A DIAMOND

[75] Inventors: Charles Eric Hunter, Hilton Head Island, S.C.; Douglas G. Waltz, Durham, N.C.

[73] Assignee: C3, Inc., Morrisville, N.C.

[21] Appl. No.: 795,228

[22] Filed: Feb. 10, 1997

Related U.S. Application Data

[63] Continuation-in-part of Ser. No. 598,564, Feb. 12, 1996, abandoned.

[51] Int. Cl.⁶ .......................... G01N 21/87; G01N 21/27
[52] U.S. Cl. .............................................. 356/30; 356/432
[58] Field of Search ........................ 356/30, 432

[56] References Cited

U.S. PATENT DOCUMENTS

| | | |
|---|---|---|
| 1,799,604 | 4/1931 | Read . |
| 2,869,417 | 1/1959 | Allen . |
| 3,610,756 | 10/1971 | Lenzen et al. . |
| 3,740,142 | 6/1973 | Takubo . |
| 3,794,424 | 2/1974 | Eickhorst et al. ........................ 356/30 |
| 4,255,962 | 3/1981 | Ashman . |
| 4,394,580 | 7/1983 | Gielisse ................................. 250/461.1 |
| 4,776,917 | 10/1988 | Ogihara et al. . |
| 4,906,083 | 3/1990 | Sattler . |
| 4,906,093 | 3/1990 | Trossarelli . |
| 4,907,875 | 3/1990 | Bowley et al. . |
| 5,118,181 | 6/1992 | Yifrach et al. . |
| 5,146,288 | 9/1992 | Russell . |
| 5,164,586 | 11/1992 | Hohberg et al. . |
| 5,260,763 | 11/1993 | Yamashita . |
| 5,379,102 | 1/1995 | Takeuchi . |
| 5,406,367 | 4/1995 | Sopori . |
| 5,468,326 | 11/1995 | Cuomo et al. ........................... 156/345 |
| 5,536,943 | 7/1996 | Smith et al. ............................... 356/30 |

FOREIGN PATENT DOCUMENTS

| | | | |
|---|---|---|---|
| 2544417 | 5/1976 | Germany ................................. 356/30 |
| 2267147 | 11/1993 | United Kingdom .................... 356/30 |

*Primary Examiner*—Richard A. Rosenberger
*Attorney, Agent, or Firm*—Richard S. Faust

[57] ABSTRACT

Diamond gemstones and gemstones formed of crystals of silicon carbide are distinguished from each other by introducing a band of ultraviolet light into a target gemstone and measuring the transmissivity of that band of light by the gemstone. A diamond will transmit light within a certain band of the ultraviolet spectrum, while a silicon carbide gemstone will block light within this band. Several instruments for carrying out this procedure are described, including an instrument that utilizes a fiberoptic strand to convey ultraviolet light that has passed through the gemstone to a solid state photodetector.

28 Claims, 19 Drawing Sheets

348
Photodetector 360
316
312
350

412
450
416
Photodetector 460

UV Light Source and Detector Located at Top of Gemstone

UV Light Source Via Flexible Cable

UV Detector Via Flexible Cable

Broad Spectrum Ultra Violet Scanning Instrument (210)

UV Transmission Natural Diamond Color G, Si2

UV Transmission 4H Silicon Carbide
Color G, Defect Level II

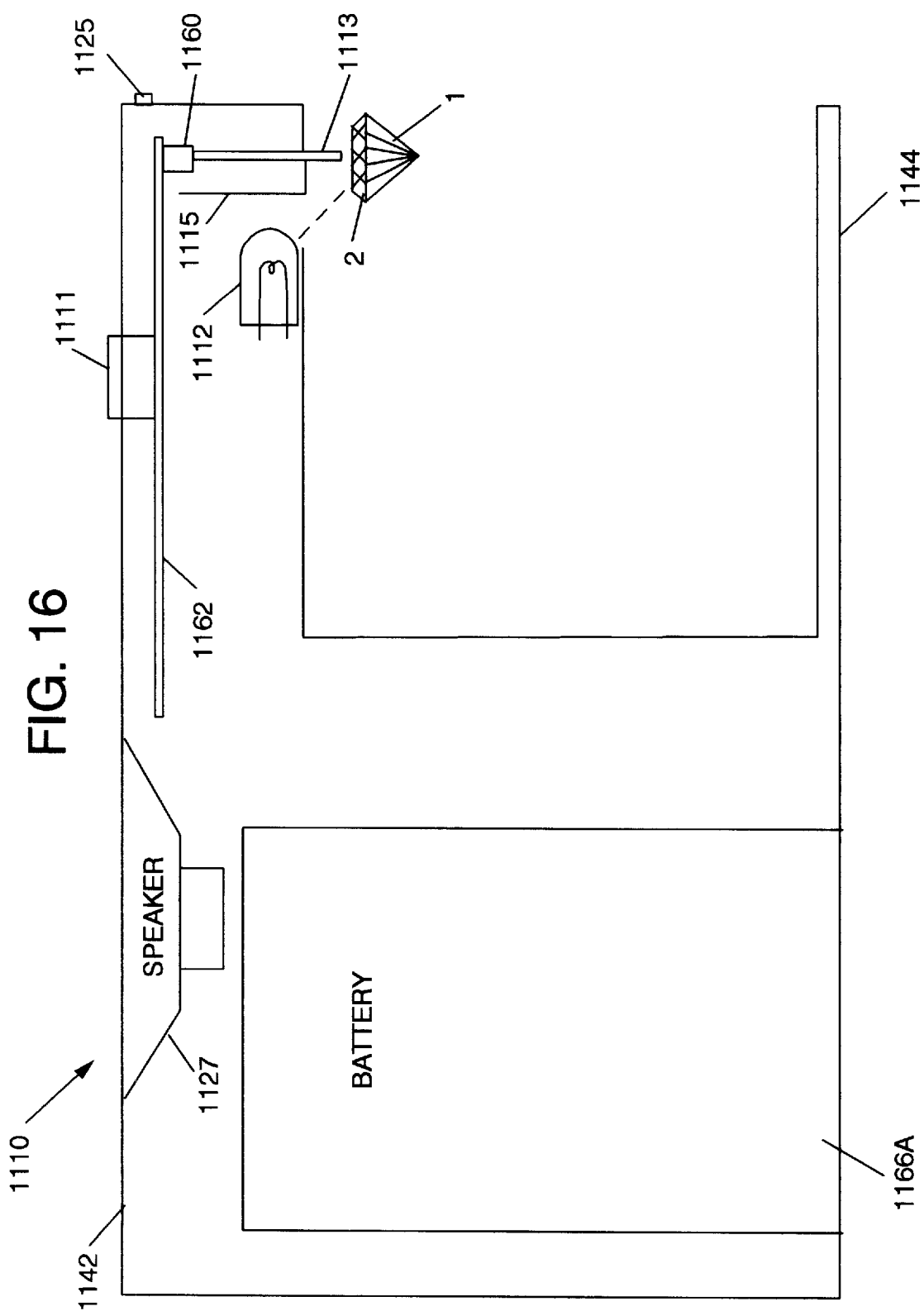

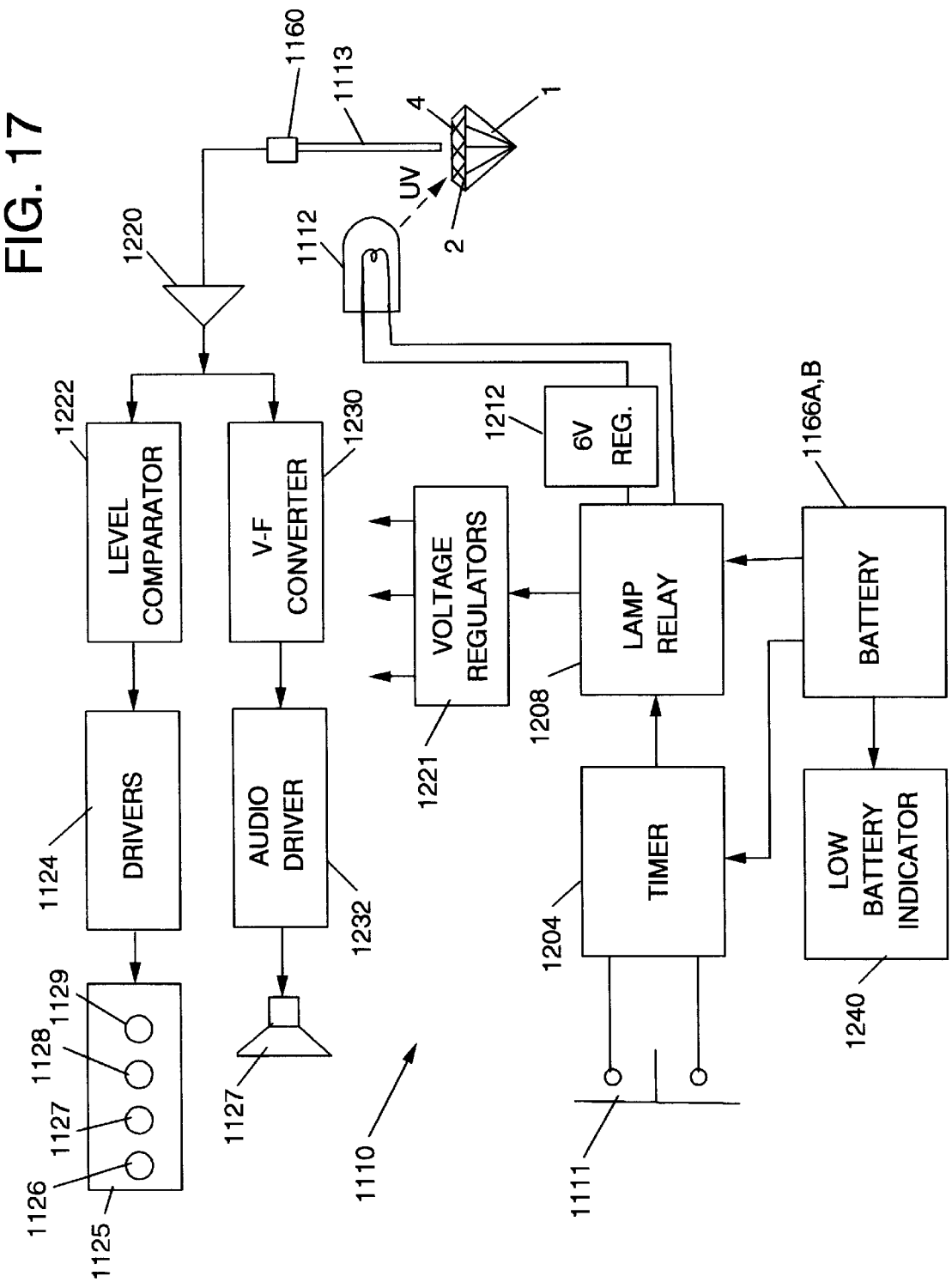

OPTICAL TESTING SYSTEM FOR DISTINGUISHING A SILICON CARBIDE GEMSTONE FROM A DIAMOND

CROSS REFERENCE TO RELATED APPLICATION

This application is a continuation-in-part of Ser. No. 08/598,564 filed Feb. 12, 1996, now abandoned.

FIELD OF THE INVENTION

The invention relates to procedures and instruments for distinguishing one material from another through nondestructive testing. More particularly, the invention relates to distinguishing between transparent/translucent materials with similar visual appearance, e.g., gemstones of similar appearance, based upon radiant energy transmission characteristics of the two materials. In preferred embodiments, the invention provides a reliable, nondestructive testing approach for determining whether a transparent colorless gemstone is diamond or moissanite (silicon carbide).

BACKGROUND OF THE INVENTION

Dating from prehistoric times, diamond has had a mythical importance to many civilizations and, as a result, has one of the highest values of all naturally occurring materials. Diamond is, of course, a crystalline form of carbon whose beauty and value derive from its extraordinary hardness, toughness and high refractive index. It is primarily the refractive index that gives diamond its characteristic brilliance.

Simulated diamond materials have entered the marketplace with varying degrees of success. The most widely distributed simulated diamond material is cubic zirconia. While cubic zirconia usually can be distinguished from diamond through visual inspection by a qualified jeweler, a test comparing physical properties of cubic zirconia versus diamond is desirable to prevent improper identification of a gemstone. In this regard, cubic zirconia has a lower refractive index than diamond. Also, it is considerably softer, has a much higher density and has a significantly lower thermal conductivity. One relatively straightforward and reliable nondestructive test for distinguishing cubic zirconia from natural diamond is set forth in U.S. Pat. No. 4,255,962 which describes an apparatus including a thermal probe held in physical contact with the gemstone being tested, and associated circuitry for determining the thermal conductivity of the gemstone.

Recently, it has been discovered that relatively low impurity, translucent or transparent single crystals of silicon carbide can be grown with desired color characteristics and thereafter cut and fashioned into synthetic gemstones. These gemstones have extraordinary hardness, toughness, chemical and thermal stability, and a high refractive index that produces unparalleled brilliance.

Silicon carbide crystals can be grown in a wide range of colors and shades within each color by the appropriate selection of dopants and by varying the net doping densities. The silicon carbide crystals can also be grown colorless or substantially colorless. Thus, silicon carbide crystals offer the potential to be cut and fashioned into gemstones of many various appearances, including that of diamond.

A comparison of certain important physical properties of diamond, silicon carbide and cubic zirconia is as follows:

| | Mohs Hardness | Refractive Index | Density (SG) | Thermal Conductivity (W/cm · K) |
|---|---|---|---|---|
| Natural Diamond | 10 | 2.42 | 3.5 | 6.6 |
| Silicon Carbide (6H polytype) | 9–9.25 | 2.69 | 3.2 | 4.9 |
| Silicon Carbide (4H polytype) | 9–9.25 | 2.71 | 3.2 | 4.9 |
| Cubic Zirconia | 7.75–8.5 | 1.98 | 5.8 | 0.02 |

Even for an experienced jeweler or diamond merchant, the difference between diamond and a colorless silicon carbide gemstone is difficult, if not impossible, to see with the naked eye. The skilled use of the usual optical tools employed in the industry still do not produce reliable results in distinguishing between the two materials. In fact, certified gemstone appraisers are known to have mistakenly identified silicon carbide as diamond. The differences that may appear in color are of no significance since silicon carbide gemstones may be produced in colorless form or with a slight tint. For example, a silicon carbide gemstone may be produced with the light shading of blue that is found in certain diamonds, including some of the rarest and most expensive diamonds, such as the Hope Diamond. As shown in the above table, the differences in hardness, refractive index, density and thermal conductivity between diamond and silicon carbide are not sufficiently great to form a basis for a reliable, easy to use testing procedure and apparatus that can be employed by typical jewelry stores and appraisers.

Other sophisticated laboratory tests might be considered for application to the problem of distinguishing silicon carbide gemstones from natural diamond gemstones. However, even many complicated and otherwise reliable techniques are limited in their application to this problem because silicon carbide can form in more than 150 different atomic arrangements (polytypes) each having different physical and electronic characteristics. In addition, the hexagonal polytypes of silicon carbide have properties that are different in each crystallographic plane. For instance, ultraviolet fluorescence of silicon carbide has little value because many silicon carbide polytypes (including 6H) do not fluoresce. Since a certain percentage of natural diamond also does not fluoresce, ultraviolet fluorescence cannot reliably distinguish between silicon carbide and diamond. Furthermore, spectrometry and x-ray techniques are not necessarily appropriate to the task because they are highly dependent on the skill of the operator and are far too complex and/or time-consuming and/or expensive to be employed on a routine basis in the tens of thousands of businesses that must now be concerned with distinguishing between diamond and silicon carbide gemstones.

With the advent of silicon carbide gemstones, and particularly colorless and lightly tinted silicon carbide gemstones, there has developed an acute need for a reliable and cost-effective procedure and apparatus for use by jewelry stores, appraisers and pawn shops to distinguish between diamond and silicon carbide gemstones, with the end goal of preventing intentional or unintentional misindentification of these valuable gemstones.

SUMMARY OF THE INVENTION

The present invention utilizes the band gap difference, and the resultant differences in radiant energy transmission characteristics of the two materials of primary interest, natural diamond gemstones and silicon carbide gemstones, to determine the identity of a gemstone being tested with exceptional accuracy. The invention may be carried out utilizing an instrument having a light source, for example, a brilliant quartz halogen incandescent lamp, that generates a spectrum of light including a discriminating band of ultraviolet energy. This energy is passed through diamond, but blocked by silicon carbide. Energy leaving the lamp is directed through a faceted gemstone, either diamond or silicon carbide, and is detected using a photodetector that has responsivity to the discriminating band of ultraviolet light (e.g. 350 nm–370 nm) within the range of about 310 nm to 400 nm. A signal is generated to drive a readout that identifies the gemstone.

In one embodiment, the instrument has a mounting cavity to place the gemstone photodetector and a lamp directly above the center of the gemstone between the lamp and the gemstone. The mask directs the energy only to the center of the gemstone cavity. The test takes only a few seconds—just long enough for the filament and detector circuit to stabilize. The lamp operates at high brilliance and, preferably, is designed for easy replacement. The instrument can operate from batteries or from a power line, with the power being required similar to that of a flashlight.

In another embodiment, the table of a target gemstone is held against the light receiving end of a light tube in the form of a fiberoptic strand, while the gemstone is illuminated by a light source. The other end of the fiberoptic strand delivers light to a solid state photodetector. The photodetector and an associated operational amplifier generate a signal to variable visual and audio outputs. This instrument may be used to carry out a method of the invention wherein a flat surface of an irradiated target gemstone is held in physical contact with the light receiving end of a light pipe while energy in the discriminating ultraviolet band is sensed in the light emanating from the opposite light emitting end of the light pipe. An output to the operator is generated with the output being variable as a function of the intensity of the ultraviolet energy in said band that is sensed. According to this method, the operator moves the target gemstone flat surface and the light receiving end of the light pipe with respect to each other to generate the highest attainable output level to verify satisfactory coupling of the light pipe to the gemstone flat surface and to thereby reliably determine the identity of the gemstone material.

The light source may take the form of an incandescent light, an arc lamp, a fluorescent light or a semiconductor device capable of emitting light (e.g., light emitting diode). The semiconductor material for solid state photodetectors of the invention may be selected from silicon, silicon carbide, gallium arsenide, gallium nitride, aluminum nitride, gallium nitride/aluminum nitride heterojunctions, gallium nitride/ aluminum nitride alloys, aluminum nitride/silicon carbide alloys or aluminum gallium nitride/gallium nitride heterojunctions. In a preferred embodiment, the photodetector active area includes a semiconductor material having a wide energy bandgap such that the photodetector has a low dark current and very high responsivity to ultraviolet light in the discriminating band.

In yet another embodiment, the invention may be defined as a method of analyzing a natural or a synthetic gemstone comprising the step of determining the optical transmissivity characteristics of the gemstone at multiple wavelengths. This method may include the step of generating a plot of radiant flux intensity vs. wavelength for multiple wavelengths for each gemstone being analyzed.

BRIEF DESCRIPTION OF THE DRAWINGS

Some of the objects having been stated, other objects will appear as the description proceeds, when taken in connection with the accompanying drawings, in which

FIG. 16 is a side view of a second tabletop instrument that is adapted to test mounted gemstones stones as well as loose stones. Portions of the housing are removed to facilitate illustration.

FIG. 17 is a block diagram of the electronics of the tabletop instrument of FIG. 16.

DESCRIPTION OF THE INVENTION

While the present invention will be described more fully hereinafter with reference to the accompanying drawings, in which aspects of the preferred manner of practicing the present invention are shown, it is to be understood at the outset of the description which follows that persons of skill in the appropriate arts may modify the invention herein described while still achieving the favorable results of this invention. Accordingly, the description which follows is to be understood as being a broad, teaching disclosure directed to persons of skill in the appropriate arts, and not as limiting upon the present invention.

Figure 1:
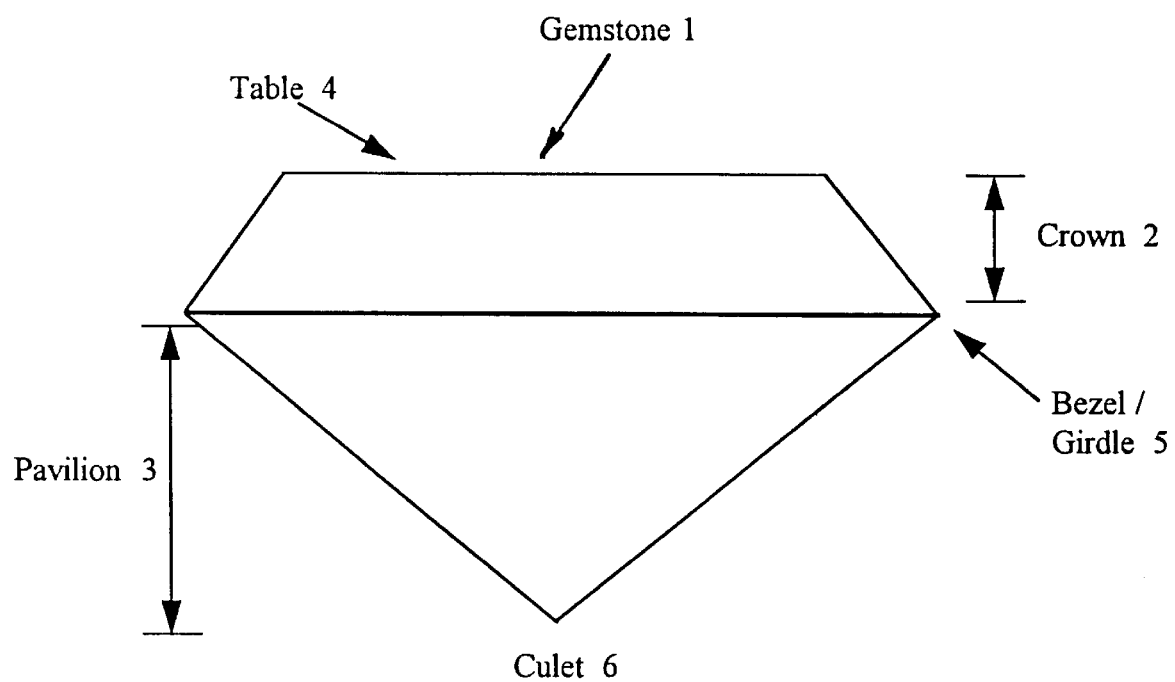
FIG. 1 is a side view of a typical round, faceted diamond with its parts labeled using terms that are common in the gemstone industry.

For purposes of clarity and to facilitate description, the present invention will be described in connection with determining light transmissivity through a typical round faceted silicon carbide gemstone or diamond such as illustrated in FIG. 1. Diamond 1 includes a crown portion 2, a pavilion portion 3, a table 4, a bezel or girdle 5 and a culet 6. It will be appreciated that other shapes of gemstones may be tested using the procedures and instruments of the present invention.

Figure 2:
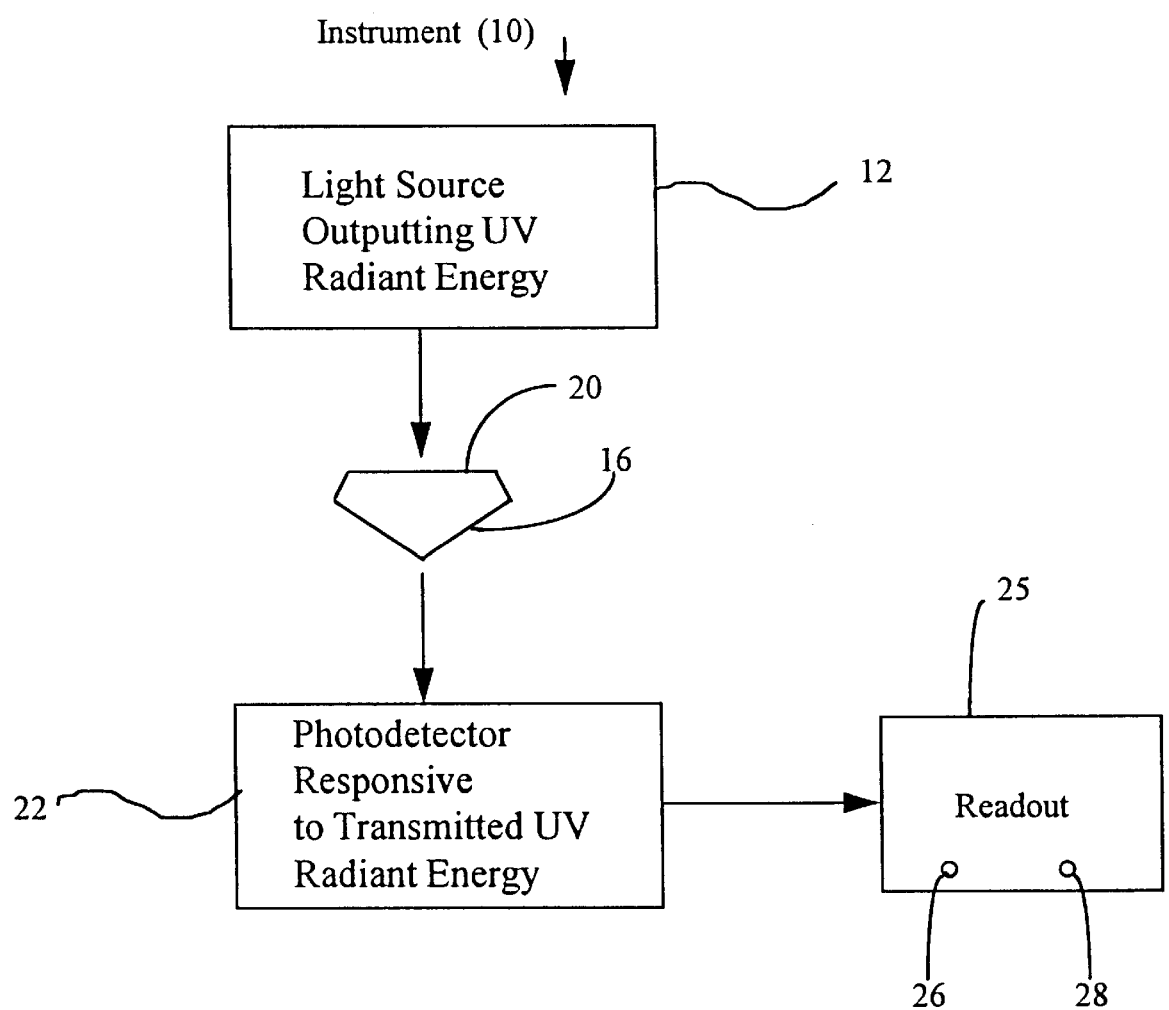
FIG. 2 is a schematic representation of an instrument of the present invention in simplified form.

General Description of Instrument for Distinguishing Diamond from Silicon Carbide Referring to the drawings, and particularly to FIG. 2, there is shown a schematic representation of an instrument 10 constructed in accordance with the present invention as applied to the task of distinguishing silicon carbide gemstones from diamond gemstones. System 10 includes a light source 12, for example, a broadband incandescent source whose output includes ultraviolet energy in a band within the range of about 310 nm to 400 nm. Light source 12 directs light to one side of a gemstone 16 that is being tested. In the simplified schematic of FIG. 2, gemstone 16 is shown as a round, brilliant cut gemstone having a table 20 that faces the light source. A photodetector 22 that is responsive to ultraviolet light resides on the opposite side of gemstone 16 from light source 12. Photodetector 22 has a known responsivity to the mentioned band of ultraviolet light that is transmitted by diamond at significantly higher levels than by silicon carbide. In this regard, ultraviolet light in the band from about 310 nanometers to 400 nanometers transmits through diamond, with a transmissivity that is a function of wavelength. On the other hand, silicon carbide, because of its more narrow energy bandgap, transmits virtually none of the light in this spectrum, i.e., the silicon carbide blocks this light. Thus, photodetector 22 is selected for having sufficient responsivity to a band of light within the mentioned ultraviolet spectrum that is transmitted by diamond but blocked by silicon carbide. Photodetector 22 produces an output signal responsive to the light within the selected band that is incident thereon as an indication of the transmissivity of the gemstone to that band of light. The output signal operates an indicator such as readout device 25 that may, in a simplified form, include two LEDs 26 and 28, one indicating diamond and the other indicating silicon carbide.

It will be appreciated that the instrument is designed so that ultraviolet light from the light source will not reach the photodetector unless it passes through the gemstone being tested. To this end, a mask (not shown in FIG. 2, but discussed in detail later in the specification) may be placed between the light source and the gemstone to direct the light only to the center of the gemstone to prevent leakage. Alternatively, light from the light source may be introduced into the gemstone by a light emitter (not shown in FIG. 2) that is in direct physical contact with the gemstone, preferably in such a fashion that it creates an optical seal.

It will be understood that the term "light" is usually used herein in a general sense to refer to both visible and invisible radiant energy. Also, the term "photodetector" is often used herein in a broad sense to refer to any light-sensitive device that can detect light within the discriminating radiant energy band used to distinguish between the materials of concern.

Light Source Characteristics

The light source may take any convenient form that will produce sufficient light in the radiant energy band that serves to distinguish the materials under consideration, in the case of diamond vs. silicon carbide, a band of light in the ultraviolet spectrum between about 310 nm and 400 nm. An incandescent light source that has sufficient ultraviolet output, such as a quartz halogen lamp or krypton lamp, may be used. An incandescent bulb has the advantage of being inexpensive and easily replaceable. Generally, an incandescent bulb will have an output including a significant amount of light outside the ultraviolet spectrum, resulting in the need, in certain embodiments, to chop the light by using a band pass filter or cutoff filter.

Certain other lamps outputting sufficient ultraviolet light may also be used, for example, a deuterium lamp.

The light source may also take the form of a semiconductor capable of emitting light (for example, LED or laser) that outputs sufficient ultraviolet light. A pn junction GaN semiconductor light emitting diode can produce a light output in the ultraviolet spectrum in a relatively narrow band of approximately 350 nm to 370 nm. Use of such a light source eliminates the need for chopping the light before it reaches the detector. Furthermore, as discussed in more detail below, this type of light source may be used in combination with a semiconductor photodetector whose peak responsivity is in approximately the same band as is emitted by the light source. For example, the above GaN light emitting diode may be matched with a GaN photodetector having a peak response at approximately 360 nm, resulting in an efficient, totally solid state instrument.

Photodetector Characteristics

The photodetector may take the form of any suitable photodetector that has sufficient response to the material-discriminating light band transmitted through the target material, and, as applied to the problem of distinguishing diamond from silicon carbide, also meets size, signal-to-noise ratio, power and other criteria appropriate to a relatively inexpensive, mass-produced instrument for the jewelry trade. In preferred embodiments, the photodetector takes the form of a semiconductor photodetector or photodetectors having sufficient responsivity to the light band being used. The preferred choice for a semiconductor photodetector is, in general, a device fabricated from a material having a wide energy bandgap such as GaN or SiC which has a low dark current (higher resolution) and high responsivity to ultraviolet light in the band. However, certain silicon (Si) photodetectors have the capability to perform satisfactory, especially if the ultraviolet light source has sufficient power and light from the source is focused into the gemstone and/or transmitted light from the gemstone is focused into the detector. Silicon detectors have the advantage of being relatively less expensive but have comparatively poor dark current and are best used with a filter to limit their response to the desired wavelength.

Silicon carbide detectors are available in sufficient size (e.g., 0.3 mm or 1 mm square) and have peak efficiency at or near 270 nm with an efficiency of about 20% to 25% at 360 nm. Also, the SiC photodetectors tend to have poor responsivity above about 400 nm and little or no responsivity above about 424 nm. The spectral response curve for SiC detectors is more favorable than Si detectors for a light band centering around 360 nm.

Other semiconductor photodetectors useful for the present invention are gallium nitride (GaN), aluminum nitride (AlN), aluminum gallium nitride/aluminum nitride (AlGaN/AlN) heterojunction, aluminum nitride/silicon carbide (AlN/SiC) alloy and aluminum nitride/gallium nitride alloy. Among these, AlGaN/AlN detectors currently under development have a peak responsivity at about 360 nm and 0% responsivity at 380 nm, and are therefore ideally suited for distinguishing between silicon carbide and diamond utilizing a discriminating ultraviolet band centering at about 360 nm.

While semiconductor photodetectors are preferred, other detectors such as an ultraviolet sensing tube or an ultraviolet sensing photomultiplier tube may be used.

It will be appreciated that the photodetector or the gemstone should be positioned carefully during the measurement, cycle to achieve maximum transmitted light impinging on the photodetector.

Chopping and Focusing the Light

In certain embodiments of the invention, when a photodetector whose spectral response curve lies totally within a relatively narrow ultraviolet band, there may be no need to chop the light. However, in those instances where the light source outputs light outside the spectrum that is blocked by the silicon carbide gemstone, and the unblocked light is also within the photodetector's response spectrum, it will be necessary to chop the light, either before it enters the gemstone or after it leaves the gemstone, before the photodetector. To this end, the light may be chopped both above and below by band pass filters. Alternatively, where the unblocked light is only above a certain wavelength, for example 390 nm, a cutoff filter may be used. Band pass filters and cutoff filters suitable for these purposes are known in the art and are commercially available.

In certain embodiments, particularly with the use of a silicon photodetector or a semiconductor photodetector having a small active area, light transmission from the source to the photodetector may be enhanced by focusing or otherwise concentrating the light. To this end, light entering or exiting the gemstone may be passed through a lens, light collimator or light concentrator.

Examples of Tabletop Instruments

Figure 3:
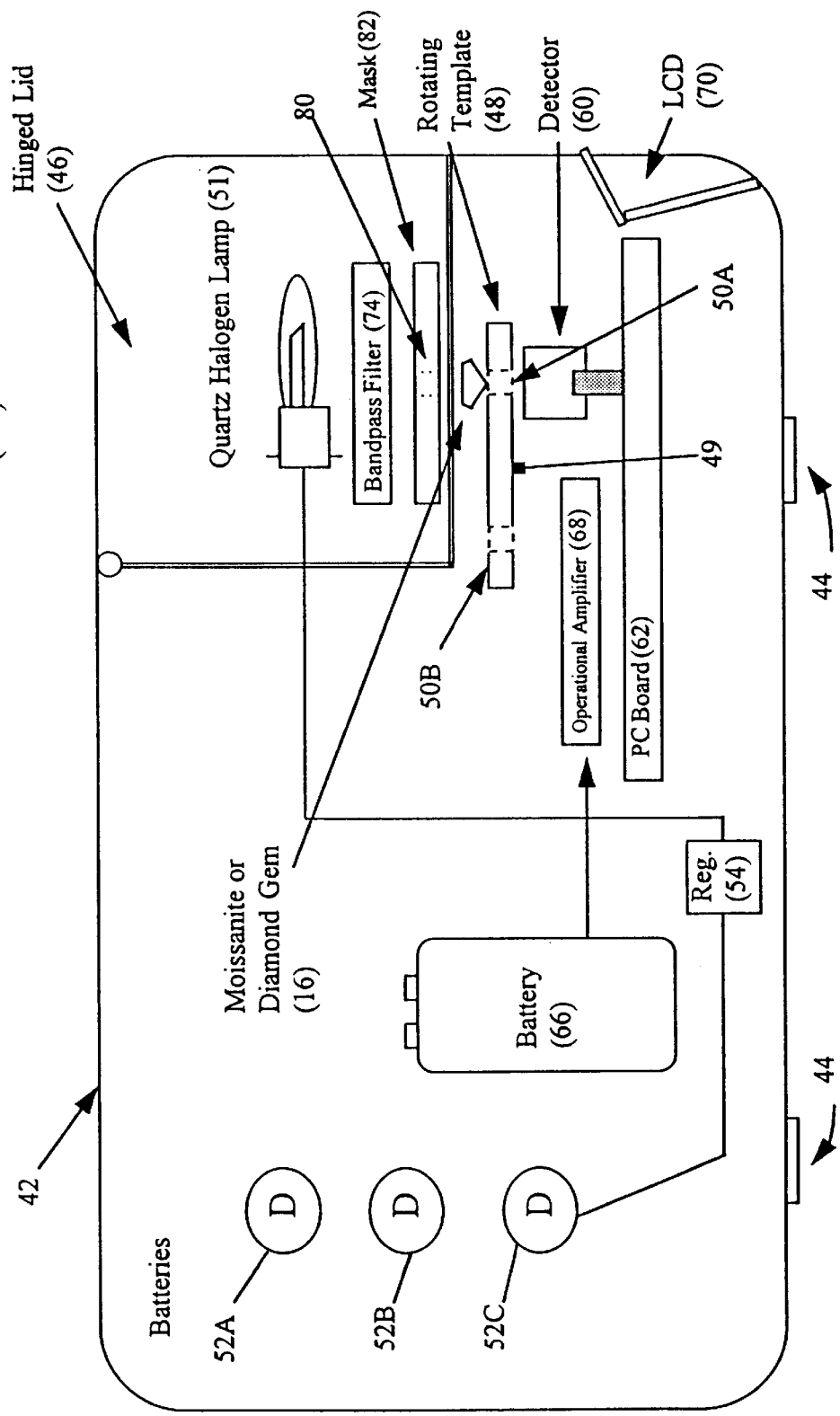
FIG. 3 is a side view of a tabletop instrument of the invention that is configured to test unmounted (loose) gemstones stones. Portions of the housing are removed to facilitate illustration.

Referring now to FIG. 3, there is shown a partly schematic, partly exploded, side view of a tabletop device 40 incorporating the principles of the present invention. Instrument 40 includes a housing 42 with a number of support legs, two of which are shown at 44. Housing 42 incorporates a hinged lid 46 that opens for loading and unloading the gemstone to be tested and remains closed during the testing operation to block out ambient light.

Instrument 40 further includes a template 48 rotatable about axis 49. Template 48 has a number of circumferentially spaced apart mounting cavities 50A, 50B, etc. for mounting gemstones of various sizes and shapes for positioning this gemstones between the light source and photodetector. As shown in FIG. 3, a gemstone 16 is mounted in an appropriately sized and shaped cavity 50A for the illustrated test. A light source in the form of a one watt quartz halogen lamp 51 is mounted within the space enclosed by hinged lid 46 in spaced relation above gemstone 16. In the illustrated embodiment, the quartz halogen lamp is powered by three D-cell batteries 52A, 52B, 52C in series through a regulator 54.

A photodetector 60 is positioned below gemstone 16 for receiving light transmitted through the gemstone and through the opening below cavity 50A that passes through to the bottom of template 48. The photodetector may take one of the forms described above, preferably one of the semiconductor photodetectors. The photodetector mounts to a PC board 62 and is powered by a battery or power source 66 and amplified by operational amplifier 68. Photodetector 60 supplies a drive signal to a liquid crystal display 70 that indicates whether the gemstone is diamond or silicon carbide.

In the illustrated embodiment, a band pass filter 741 is positioned directly below the light source to pass only a selected band of light within the ultraviolet range. In one embodiment, the band pass filter takes the form of a ten nanometer band width FWHM (full width half maximum) filter centering at 360 nanometers, resulting in a passed band of ultraviolet energy in the range of approximately 355 nanometers to 365 nanometers. The light, so chopped, passes through an opening 80 in a mask 82 that resides directly above gemstone 16. The mask directs the ultraviolet energy only to the center of the gemstone to prevent energy leakage around the mounting cavity.

In one embodiment, the photodetector may take the form of a silicon carbide detector model no. CD-260-1-00-D manufactured by Cree Research, Inc. of Durham, N.C., USA. This detector has sufficient responsivity in the mentioned 355–365 nanometer range.

A second tabletop instrument 1110 for distinguishing between diamond and silicon carbide gemstones stones will now be described with reference to FIGS. 16–18. Instrument 1110 includes a housing 1142, portions of which are removed in FIG. 16 to facilitate illustration. In a preferred embodiment, housing 1142 is formed of rigid plastic and painted with a nickel acrylic or carbon barrier material to block electrical noise that may interfere with the sensitive circuitry of instrument. Instrument 1110 has a base portion 1144 for supporting the instrument on a tabletop or other level surface. The primary components within or supported by housing 1142 are switch 1111, batteries 1166A, 1166B (only one shown), lamp 1112, fiberoptic strand 1113, fiberoptic shield 1115, ultraviolet photodetector 1160, printed circuit board 1162, LED readout 1125 and speaker 1127.

A simplified description of the operation of instrument 1110 is as follows: First, the operator presses switch 1111 to turn on the instrument, including lamp 1112. Next, the flat table 4 of a gemstone 1 is manually held in physical contact with the lower light receiving end of a light tube that takes the form of a fiberoptic strand 1113 that protrudes approximately ⅜ inch from its shield. Reflected ultraviolet energy that enters the fiberoptic strand is emitted at the opposite light emitting end of the strand onto a solid state ultraviolet photodetector 1160. If the gemstone is silicon carbide, the ultraviolet energy is absorbed in the gemstone, resulting in no reflected ultraviolet energy entering fiberoptic strand 1113 and no output signal from the photodetector and its associated operational amplifier 1220. If the gemstone is diamond, the photodetector/amplifier produces a signal that is processed to create (i) a variable visual output by lighting one or more of a series of LED's 1125 and (ii) a variable audio output that increases in pitch as the intensity of ultraviolet energy to the photodetector increases. The variable visual and audio outputs encourage the operator to move the target gemstone's flat table with respect to the light receiving end of strand 1113 to generate the highest attainable output level to verify satisfactory coupling of the strand to the gemstone table and to thereby reliably determine the identity of the gemstone material.

Referring to FIG. 17, switch 1111 is a conventional momentary switch that serves to actuate instrument 1110 for a selected time duration, e.g. 25 seconds, as determined by a timer 1204. Batteries 1166A, B are conventional six volt lantern batteries that supply power to lamp 1112 through a lamp relay 1208 and a six volt regulator 1212. The weight of the lantern batteries tends to stabilize instrument 1110. Lamp 1112 preferably takes the form of a six volt, one amp, low wattage quartz halogen lamp.

Light from lamp 1112 enters gemstone 1 primarily through the crown 2 and, by internal reflection, a portion of the light emerges from table 4. It is this reflected light that: enters the light receiving end of fiberoptic strand 1113. While not illustrated, strand 1113 may be encased in a protective sleeve, such as a stainless steel sleeve. Strand 1113 may take the form of a 0.041 inch (1.04 mm) diameter strand of conventional construction, e.g. a solid quartz strand manufactured by General Fiber Optics, Inc. of Fairfield, N.J., USA, under model no. 16-0800-HNS-C22-X.0057-P/2. Light: emanating from the upper light emitting end of strand 1113 is incident upon photodetector 1160 which, in this embodiment, takes the form of a model no. CD-260-0.30-D silicon carbide ultraviolet photodetector chip manufactured by Cree Research, Inc. of Durham, N.C., USA. This particular photodetector 1160 has a 300 $\mu$m×300 $\mu$m square die shape which conforms well to the light output pattern emanating from fiberoptic strand 1113. As discussed in more detail below, this photodetector 1160 is used in its photoconductive mode, so that with no ultraviolet light present, the photodetector presents an open circuit. With increasing ultraviolet light incident thereon, the resistance decreases so that photodetector 1160 has a variable resistance as a function of incident ultraviolet light. Due to its very high sensitivity, photodetector 1160 produces an output signal on the order of 6 picoamps.

Coupled to photodetector 1160 is an operational amplifier 1220 that provides a variable voltage output to both the visual and audio output circuits. Both the visual and audio output circuits are powered from batteries 1166A,B through conventional voltage regulators 1221.

The visual output circuit includes a level comparator 1222 and LED drivers 1224 that drive the four LED's 1126, 1127, 1128, 1129 of LED readout 1125.

The audio output circuit includes a voltage-to-frequency (V-F) converter 1230 and an audio driver 1232 that produces a variable drive to speaker 1127.

The schematic diagram of FIG. 18 presents more detail of the circuitry of instrument 1110. While FIG. 18 is believed to be largely self-explanatory to one of skill in the art, several features will be discussed. With respect to the operation of lamp 1112, a 12 volt battery power supply connects to the lamp through a six volt regulator 1212 to assure that a uniform voltage is supplied to the lamp even after the battery has been substantially drained. It is desirable for the lamp to always operate at the same voltage so that its output will be consistent. A conventional low battery indicator 1240 is provided, however, to sense a battery voltage below approximately nine volts.

As mentioned above, the solid state photodetector 1160, while capable of producing an output in either a photovoltaic mode or a photoconductive mode, is used in the photoconductive mode wherein a five volt source to the photodetector is conducted variably by the photodetector with the output to the operational amplifier (IC1) 1220. Output from operational amplifier 1220 is delivered to both the visual and audio output circuits.

In the visual output circuit, level comparator 1222 takes the form of a quad comparator (IC3) of conventional design that has four amplifiers biased at different voltage levels. Level comparator 1222 is connected to LED drivers 1224 that take the form of a conventional quad LED driver (IC4).

In the audio output circuit, the V-F converter 1230 (IC2) takes the form of a model no. AD654 converter manufactured by Analog Devices of Norwood, Mass., USA. The output of V-F converter 1230 is delivered to a simple audio driver 1232 that drives speaker 1127 so that the pitch of the audio output increases as the level of ultraviolet light incident on photodetector 1160 increases.

It will be appreciated that the term "light tube" is sometimes used herein to refer to a suitable light conveying member capable of receiving ultraviolet light that has passed through the target gemstone and conveying the light to the photodetector. The particular type of light tube used in the embodiment of FIGS. 16–18 is a fiberoptic strand, preferably a solid quartz strand that will transmit ultraviolet light at up to approximately 90% efficiency.

The cross-sectional area of the light tube is important, particularly when a fiberoptic strand is used. It is desirable for an instrument of the present invention to be capable of use with gemstones stones having a size as small as about 1/10 carat. A 1/10 carat diamond or silicon carbide gemstone cut as a brilliant round stone will have a table that is approximately 0.065 inch (1.65 mm) across. Thus, the diameter of a fiberoptic strand used in accordance with the invention most preferably should be sized so that it can completely fit on the table of such a stone. Another consideration with respect to fiberoptic strand size is that larger strands have less tendency to be broken in use and convey more light to the photodetector. As mentioned above, the preferred size for fiberoptic strand 1113 of FIGS. 16–18 is 0.041 inch which permits the strand to fit on the table of a 1/10 carat stone. In practice, fiberoptic strands having a diameter in the range from about 0.015 inch (0.38 mm) to 0.080 inch (2.03 mm) are workable, while a more preferred diameter range is from about 0.030 inch (0.76 mm) to 0.060 inch (1.52 mm). While the task of properly placing such strands on the relatively small tables of gemstones, particularly gemstones stones as small as 1/10 carat, may seem a daunting task, it will be appreciated that the variable output (visual and/or audio) permits the operator to move the light receiving end of the fiberoptic strand on the table until the operator hits the locations that produce the highest attainable output level, thereby verifying the satisfactory coupling of the fiberoptic strand to the gemstone table and to assure reliable identification of the gemstone material. This feature of the invention, as made possible by embodiments such as the one shown in FIGS. 16–18, greatly increases the ease of use of the invention, particularly by relatively non-scientific, untrained operators, and also greatly decreases the chance of false readings, even for the most skilled operators.

A further consideration with respect to sizing of instrument components is that preferably the photodetector active area (the active semiconductor layer in the case of a solid state semiconductor photodetector) should be sized to roughly correspond to the area of light output that is incident thereon. In the case of an instrument using fiberoptic strands as described above, the light output area will be on the order of 0.02 inch to 0.10 inch in diameter. The preferred silicon carbide photodetector referred to above has an active area on the order of only about 5% to 30% of this light pattern; however, the remarkably high responsivity of the silicon carbide photodetector permits its use even when as little as about 5–10% of the light from the fiberoptic strand actually impinges on the active area. As an alternative embodiment, a lens, light collimator or light concentrator may be located between the light emitting end of the strand and the photodetector to focus a significantly greater portion of the light on the active area of the photodetector. As another alternative, a photodetector with a larger active area may be used, for example, a model no. CD-260-1.00-D silicon carbide ultraviolet photodetector chip manufactured by Cree Research, Inc. of Durham, N.C., USA. This photodetector has an active area on the order of 0.00965 $cm^2$. In general practice of the invention with light tubes as discussed above, an active area in the range from about 0.0005 $cm^2$ to 0.05 $cm^2$ is suitable.

It is important that the amount of light impinging on the active area of the photodetector and the responsivity of the photodetector, taken together, be sufficient to generate a sufficient signal to reliably discriminate between silicon carbide and diamond gemstones utilizing conventional, relatively inexpensive circuitry components available to the electronics designer. Since the size of the fiberoptic strand is largely determined by gemstone table size and the intensity of the light instant on the gemstone is limited by considerations of lamp power consumption, heat generation, etc., the photodetector must operate above a responsivity level that is largely determined by fiberoptic strand size and gemstone size. It has been found that under short circuit current conditions the responsivity of the photodetector to light in the discriminating band of ultraviolet light should be greater than about 2 mA/W, preferably greater than about 10 mA/W and most preferably greater than about 20 mA/W.

Leakage of the photodetector under dark current test: conditions ($V=^-1V$ at 25° C.) should be low enough to permit reliable operation of the instrument without "false diamond" readings. A dark current lower than about one picoamp is desirable with dark currents lower than about one fentoamp being most preferred.

Example of Hand Held Instrument

Figure 4:
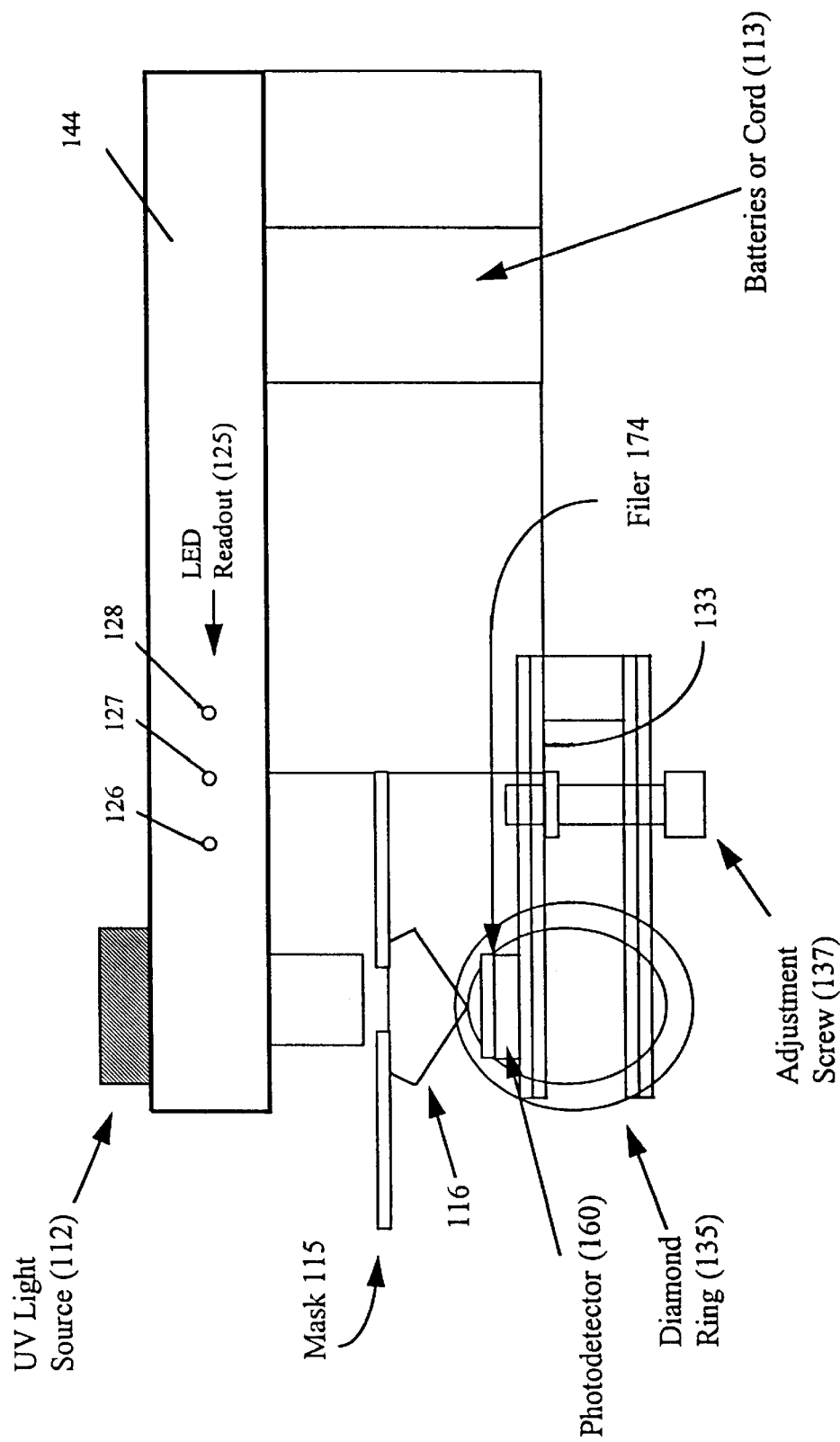
FIG. 4 is a side view of a hand held instrument of the invention configured to test mounted gemstones stones.

Referring now to FIG. 4, there is shown a schematic view of a hand held, easily portable instrument 110 that has a gemstone holding configuration for testing mounted gemstones. In this regard, it should be noted that embodiments of the invention that incorporate a gemstone holding mechanism may be designed for use with either loose or mounted gemstones, as desired.

Instrument 110 includes a housing 144 containing a light source 112, a mask 115, a battery compartment 113, a readout device 125 with LEDs 126, 127, 128, and a mechanical support 133 for supporting a diamond ring 135 with the mounted gemstone 116 directly below the light source. Mechanical support 133 carries a photodetector 160 and overlying band pass filter 174.

Mechanical support 133 may take any convenient form that supports the ring in such a way that light can pass through the gemstone to the photodetector as required by the present invention. In the illustrated embodiment, an adjustment screw 137 is used as a means for engaging and locking the ring in position.

Figure 5:
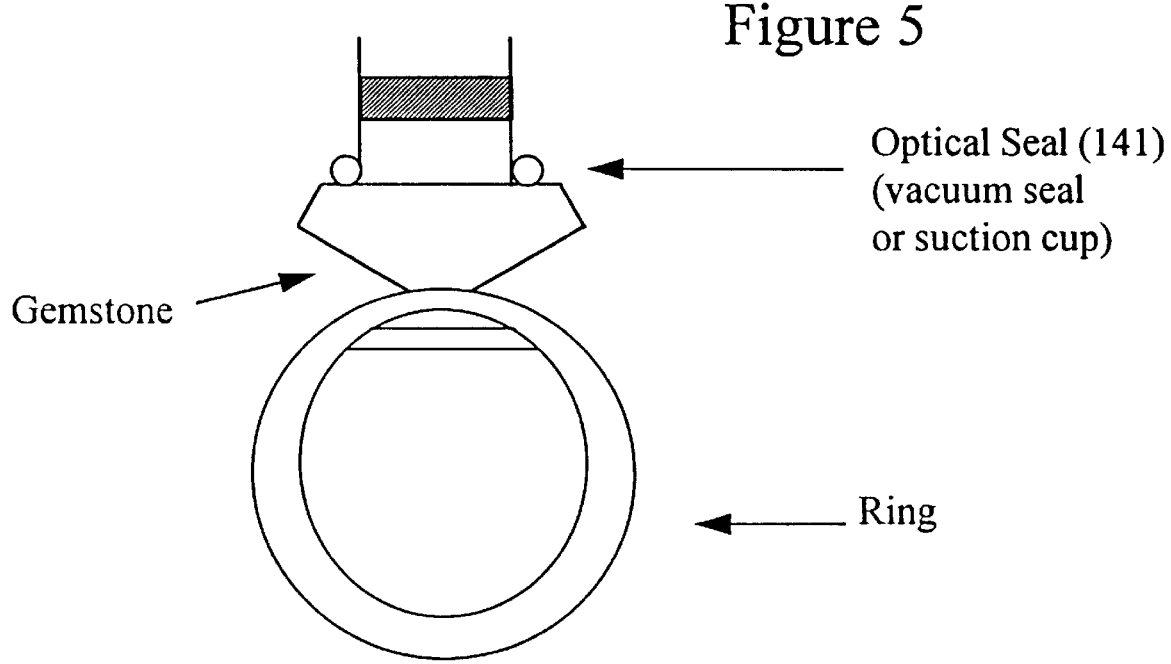
FIG. 5 is an enlarged view of an optical seal for use in an instrument similar to that of FIG. 4 as used to seal the light tube to the table of the diamond in order to prevent light from reaching the detector without first passing through the gemstone.

FIG. 5 illustrates an alternative arrangement for a hand held instrument as shown in FIG. 4 wherein the light source is shown mounted to the gemstone with an optical seal 141 made with a vacuum seal or suction cup. Other sealing arrangements include wax, grease or other media that prevent light leakage. It will be appreciated that as a further optional arrangement, the photodetector may be optically sealed to the gemstone, e.g., at the gemstone table as shown in FIG. 5, with the light entering the gemstone through the pavilion.

Figure 6:
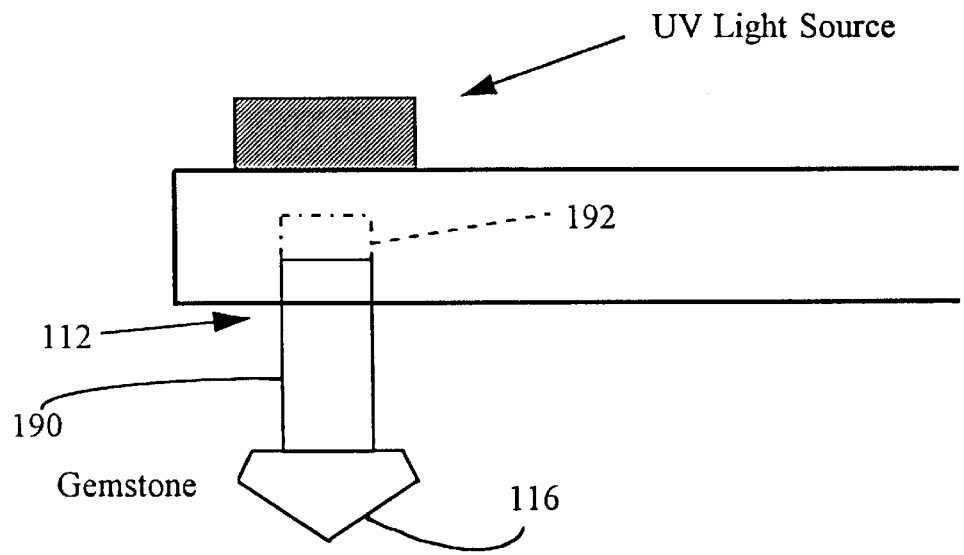
FIG. 6 is an enlarged view of the pressure activated light emitter of the instrument illustrated in FIG. 5.

In the embodiment illustrated in FIG. 6, the light source includes a light emitter 190 in physical contact with gemstone 116 to form an optical seal. The light source is energized through a pressure sensitive switch 192 activated by contacting the light emitter to the gemstone. The light emitter may take the form of a light tube such as fiberoptic as are known in the art, or other suitable form.

Other Instrument Configurations

Figure 7:
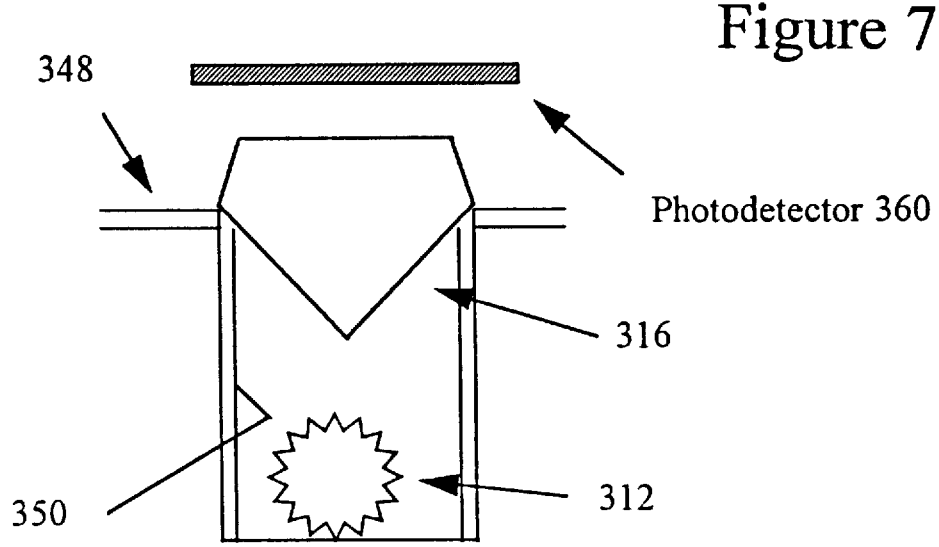
FIG. 7 is a side view of a portion of an instrument of the invention wherein light is introduced into the gemstone through the bottom angled facets (pavilion) and is detected as it leaves the gemstone at the crown.

FIG. 7 is a schematic representation of a portion of another instrument of the invention showing an alternative structure for light transmission and detection. In this embodiment, gemstone 316 is supported by a template 348. Light source 312 is contained within a light pipe 350 that preferably has an internal reflective coating. Light pipe 350 is optically sealed to the pavilion portion of the gemstone just below the girdle by any of the means discussed above, such as a vacuum seal. A photodetector 360 is positioned above the gemstone table to receive light transmitted through the gemstone.

Figure 8:
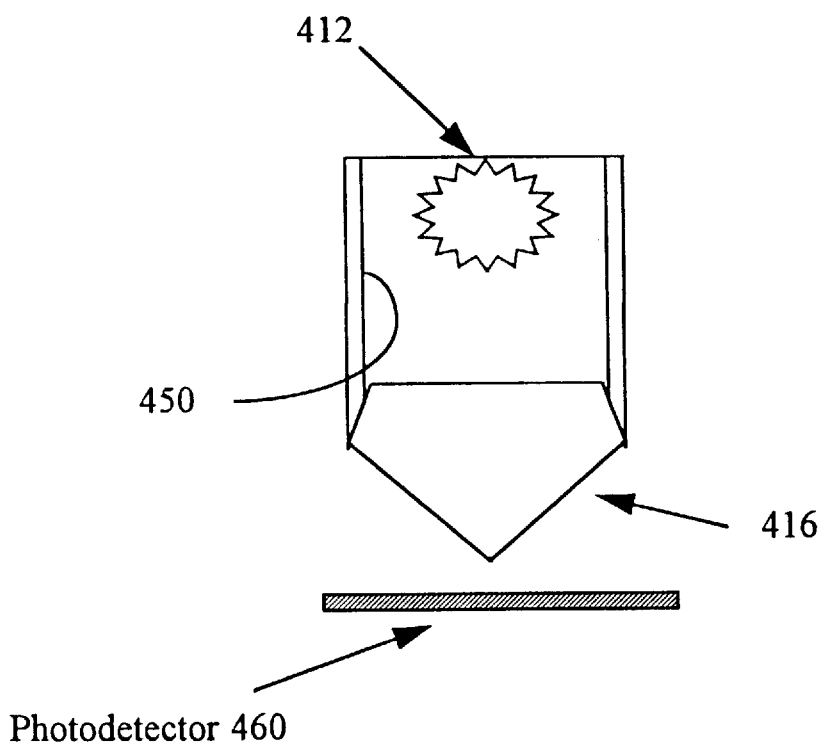
FIG. 8 is a view similar to FIG. 7 but showing light introduced into the gemstone through the table, with the light being detected as it leaves the pavilion.

FIG. 8 shows an arrangement similar to that of FIG. 7 except that light pipe 450 encasing light source 412 is optically sealed to the gemstone at the crown, just above the girdle. A photodetector 460 is positioned under the gemstone pavilion.

Figure 9:
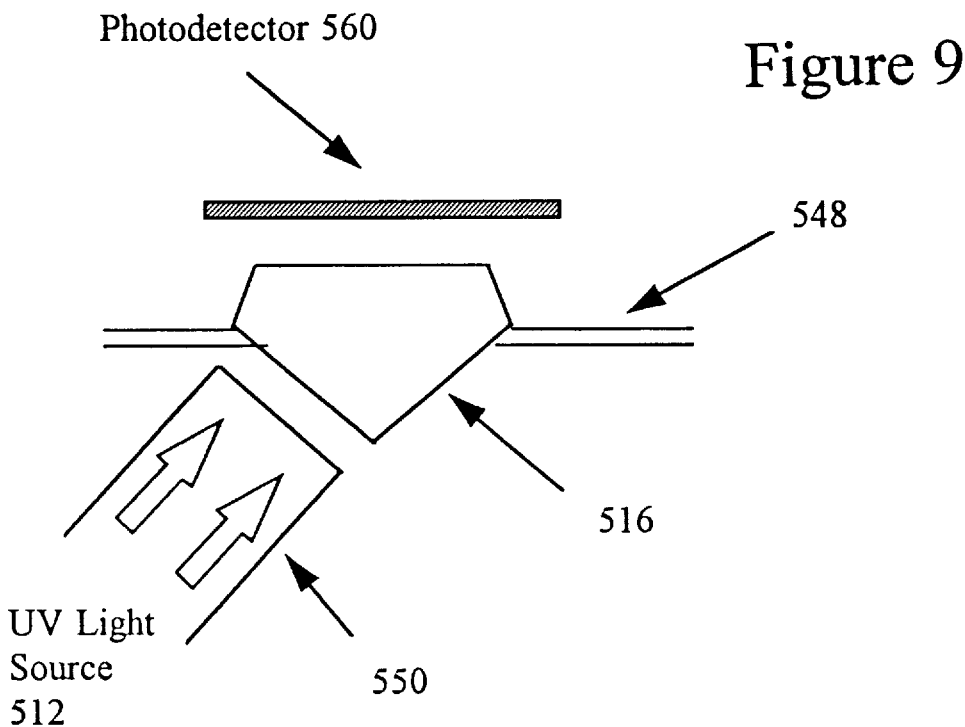
FIG. 9 is a side view of a portion of another instrument of the invention wherein light is introduced into the gemstone through the bottom angled facets (pavilion) by a light tube, light pipe or fiber optic source.

FIG. 9 is a schematic representation of a portion of yet another embodiment of the invention. Gemstone 516 is supported by a template 548. A light source 512 provides a direct beam of light aimed at the angled facets of the gemstone pavilion. In this embodiment, the light emitter may take the form of a light tube (e.g., a quartz rod that carries light), a light pipe with internal reflective coating or a fiber optic cable. A photodetector 560 is positioned above the gemstone table.

Figure 10:
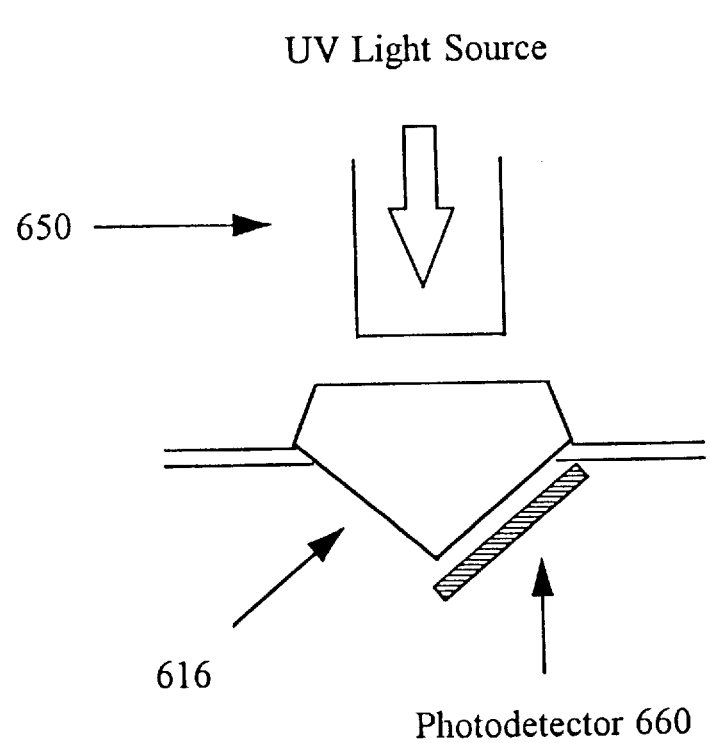
FIG. 10 is a view similar to FIG. 9 showing light entering the gemstone at the table and being detected at the angled facets of the pavilion.

FIG. 10 shows an arrangement similar to that of FIG. 9 except that the light emitter, in the form of a light tube, light pipe or fiber optic cable, terminates directly above the table of the gemstone for introducing light through the table. A photodetector 660 is positioned to receive light from the angled facets of the pavilion.

Figure 11:
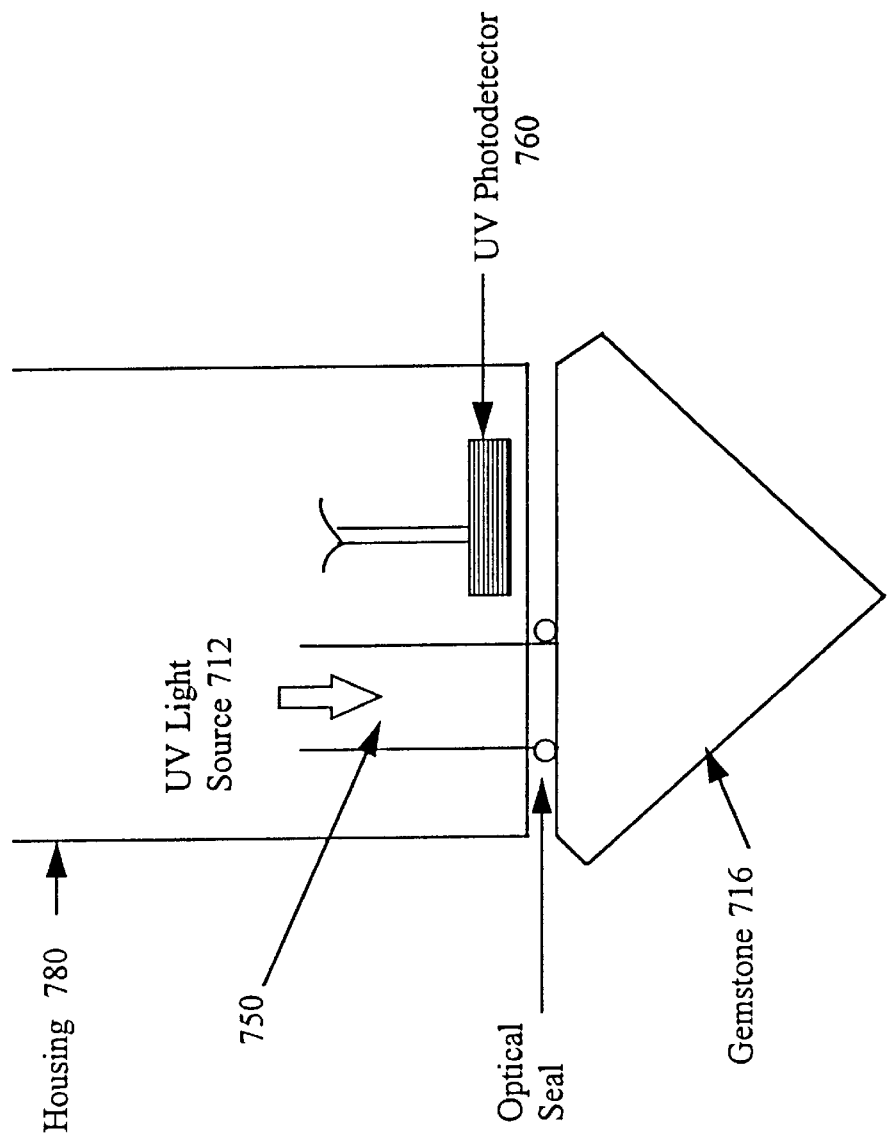
FIG. 11 is a side view of yet another embodiment of the invention where light is introduced into the gemstone by a light tube optically sealed to the gemstone table and light is detected as it exits the gemstone through the crown.

FIG. 11 is a schematic representation of another alternative embodiment of the invention including a light tube 750 optically sealed to a portion of the table of gemstone 716. A photodetector 760 is positioned next to the terminal end portion of light tube 750 for receiving light reflected back from within the gemstone. Both light tube 750 and photodetector 760 are contained within a housing 780. According to this embodiment, the instrument may serve as a probe-type device wherein the light tube is brought into direct contact with the gemstone with a photodetector contained within the same probe housing. Thus, according to this embodiment, the instrument does not need to include a mechanical support for the gemstone.

Figure 12:
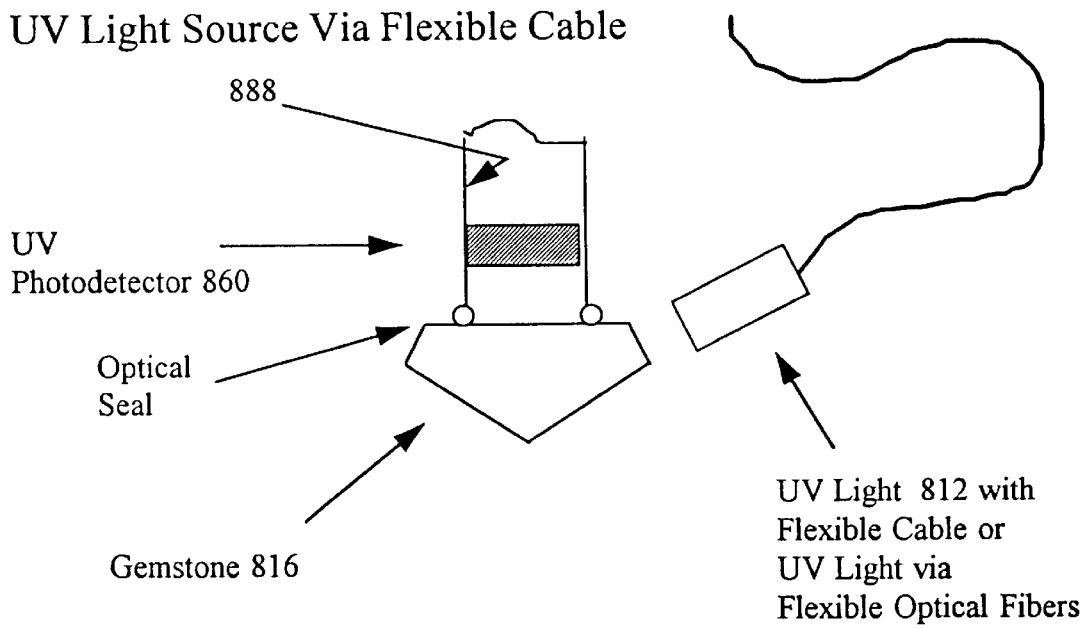
FIG. 12 is a side view of a portion of another instrument of the invention wherein the photodetector is encased in a tube that is optically sealed to the table of the gemstone with the light introduced into the stone by a hand-controlled light source on a flexible cable.

FIG. 12 is a schematic representation of another embodiment of the invention wherein photodetector 860 is contained within a tubular structure 888 optically sealed to the table of gemstone 816. The tubular structure 888 may take the form of a probe emanating from a hand held instrument. The light source 812 is contained within a hand held unit which may be manually moved around the pavilion and crown surfaces of the stone during the testing operation.

Figure 13:
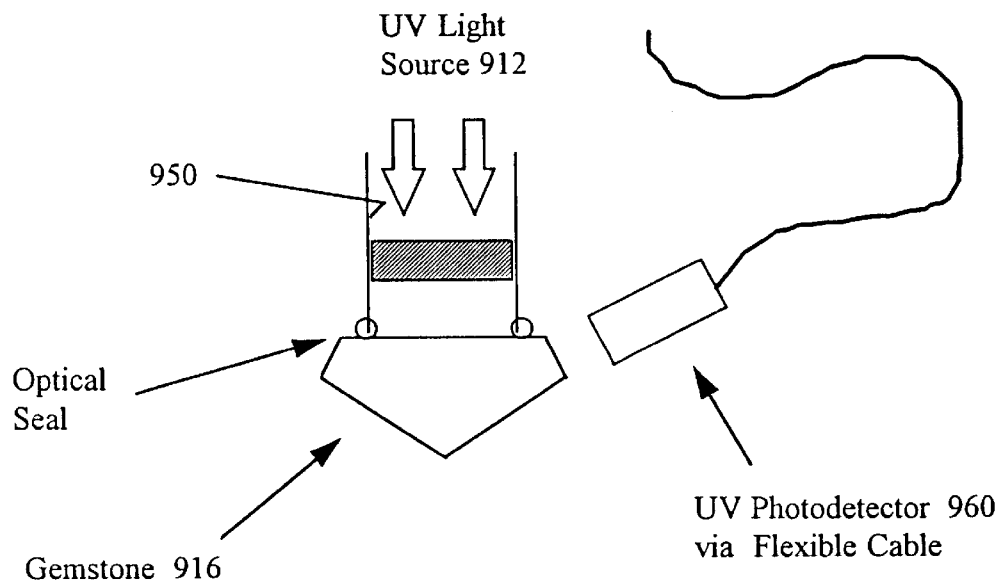
FIG. 13 is a view similar to FIG. 12 showing an instrument wherein the light source is encased in a tube that is optically sealed to the table of the gemstone with the photodetector incorporated into a hand-controlled device on a flexible cable.

FIG. 13 illustrates a device similar to that of FIG. 12 except that the light source 912 is contained within a light tube 950 that is optically sealed to the crown of gemstone 916. The photodetector 960 is contained within a manually held unit which can be moved about the gemstone pavilion and crown surfaces for detection of light during the testing operation.

It will be appreciated that the tubular structure 888 of FIG. 12 and the light tube 950 of FIG. 13 may be optically sealed to the angled facets of the pavilion instead of to the table and still be used in connection with a hand held and movable light source or photodetector as shown.

Broad Spectrum Ultraviolet Scanning Instrument

A more accurate analysis of gemstones can be performed by using a series of band pass filters and calibrated detectors to determine the optical transmissivity characteristics of a given gemstone at several wavelengths. This information more fully characterizes a natural or synthetic gemstone.

Figure 14:
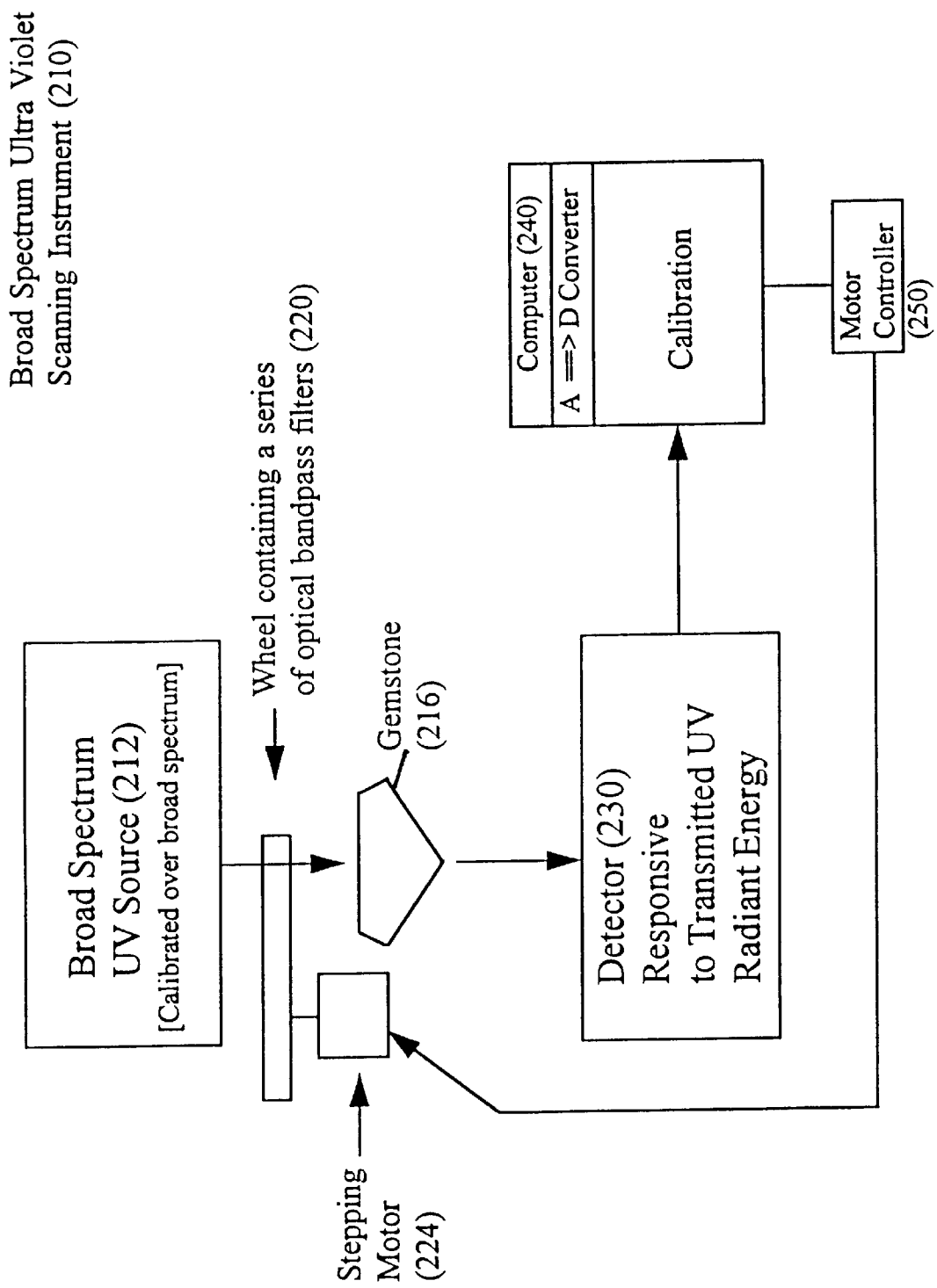
FIG. 14 is a schematic representation of an apparatus of the invention for scanning multiple bands of ultraviolet transmission.

Referring to FIG. 14, there is shown an apparatus 210 having light source 212 that outputs a broad spectrum of wavelengths, preferably including ultraviolet, and is calibrated to known standards. A series of circumferentially spaced apart band pass filters (not shown in detail) is mounted in a horizontally disposed wheel 220 such that each filter can be individually positioned under the light source. Filter positioning can be done manually, but is preferably done by a computer controlled stepping motor 224. A target gemstone 216 is mounted under filter wheel 220. Radiant energy from the source passes through each filter, the gemstone and onto the detector. The detector may consist of a photomultiplier tube or a series of semiconductor detectors that are calibrated to known sources. Though all mechanical motions of instrument 210 and all calculations can be done manually, a modern instrument would be computer driven and such a system is shown in FIG. 14 and described below.

Broad spectrum light sources usually are lamps and would normally contain a combination of gases to provide a smoothing effect to the output spectrum. Typical gasses are deuterium or a combination of mercury and xenon. Narrow bandwidth filters (such as 10 or 20 nanometer types) are usually interference type filters. The most broad spectrum detector known is the photomultiplier tube. It is rather bulky, requires considerable support electronics, is very expensive, but is an acceptable instrument for precision work. Diffraction gratings and semiconductor photodetectors can be combined to make a broad range detector. Alternately, individual calibrated detectors can be used for different parts of the spectrum.

Figure 15A:
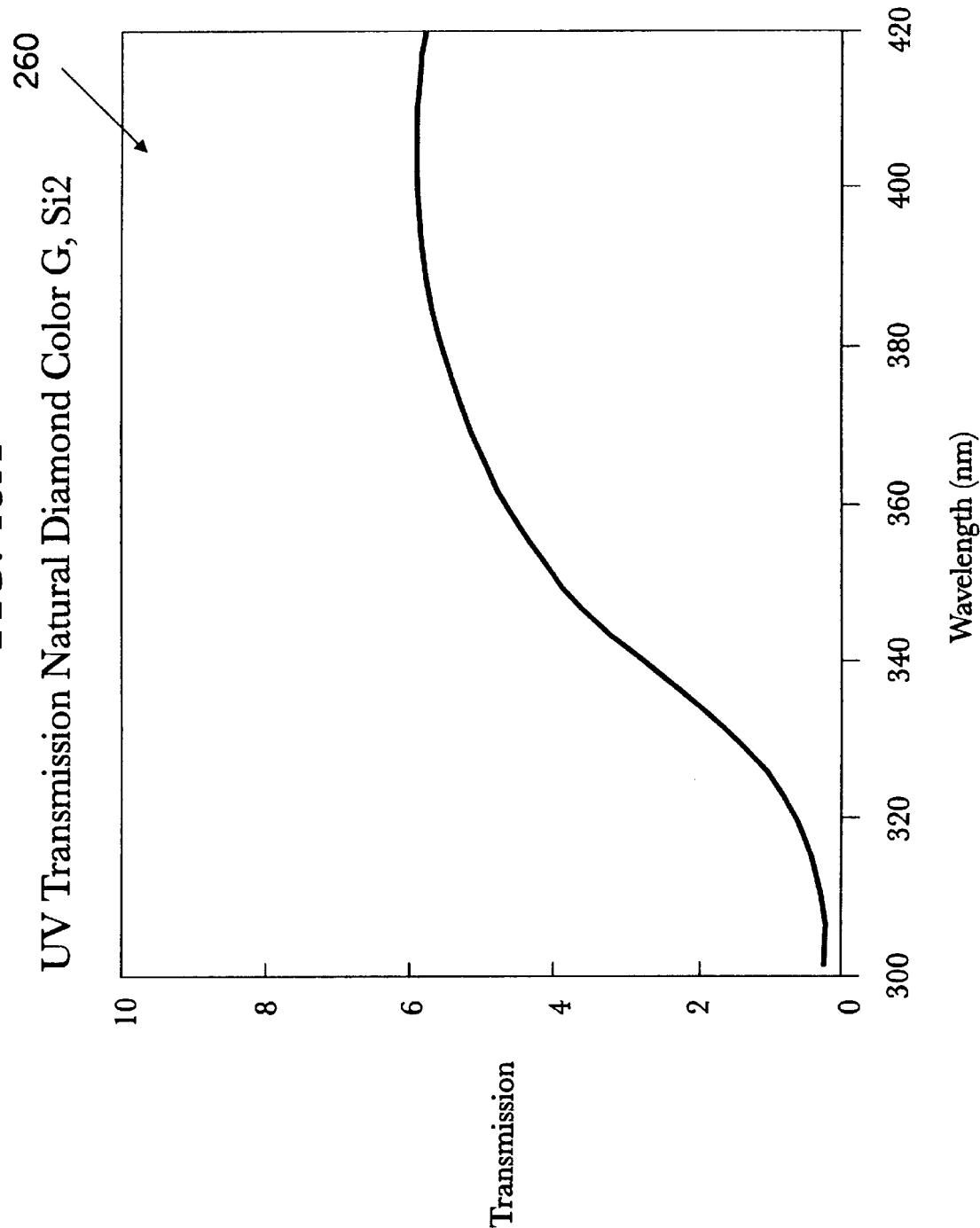
FIGS. 15A and 15B are graphs generated by the apparatus of FIG. 14. The graphs show radiant flux intensity plotted vs. wavelength for a diamond gemstone and silicon carbide gemstone, respectively.
Figure 15B:
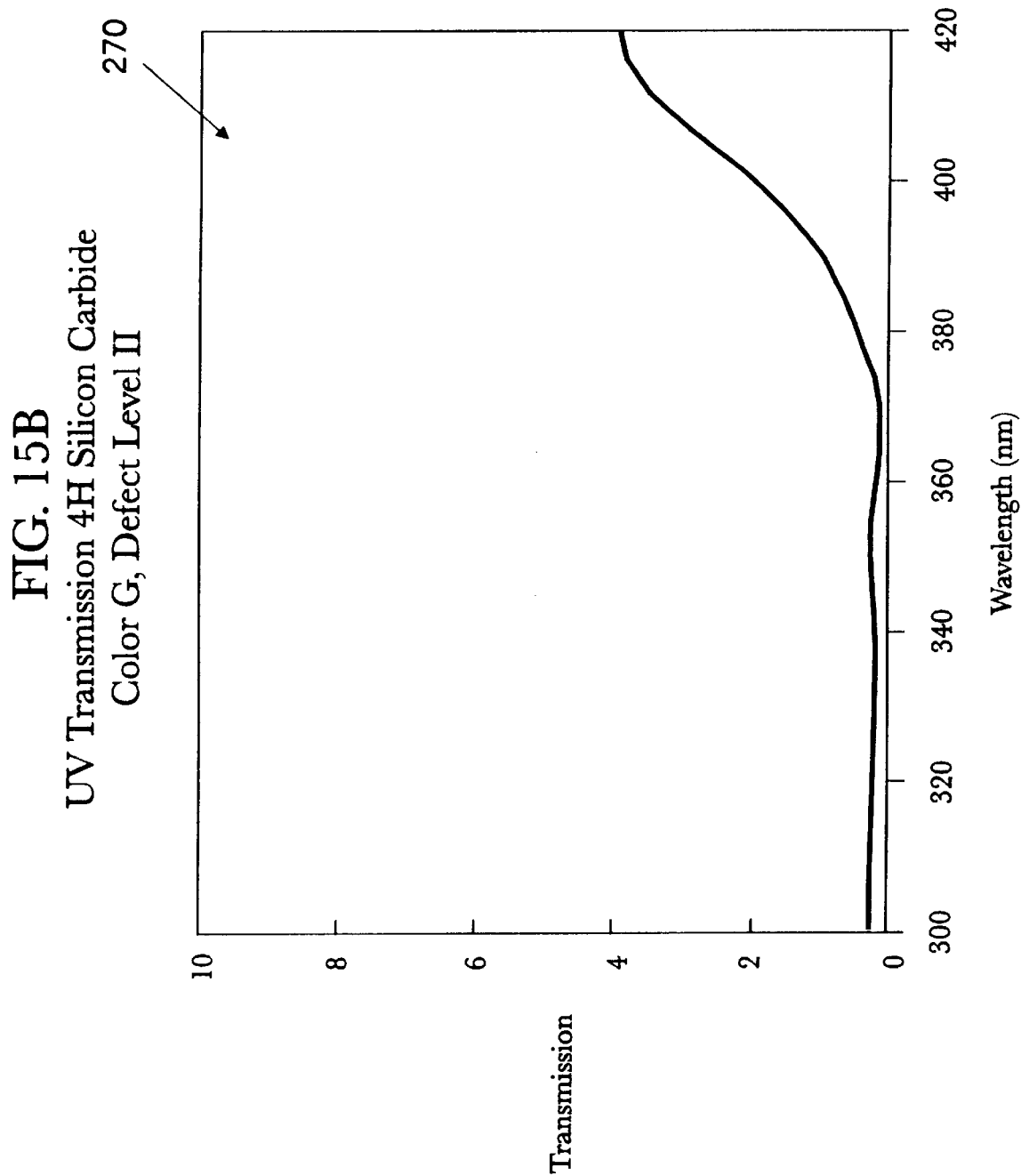
Figure 18A:
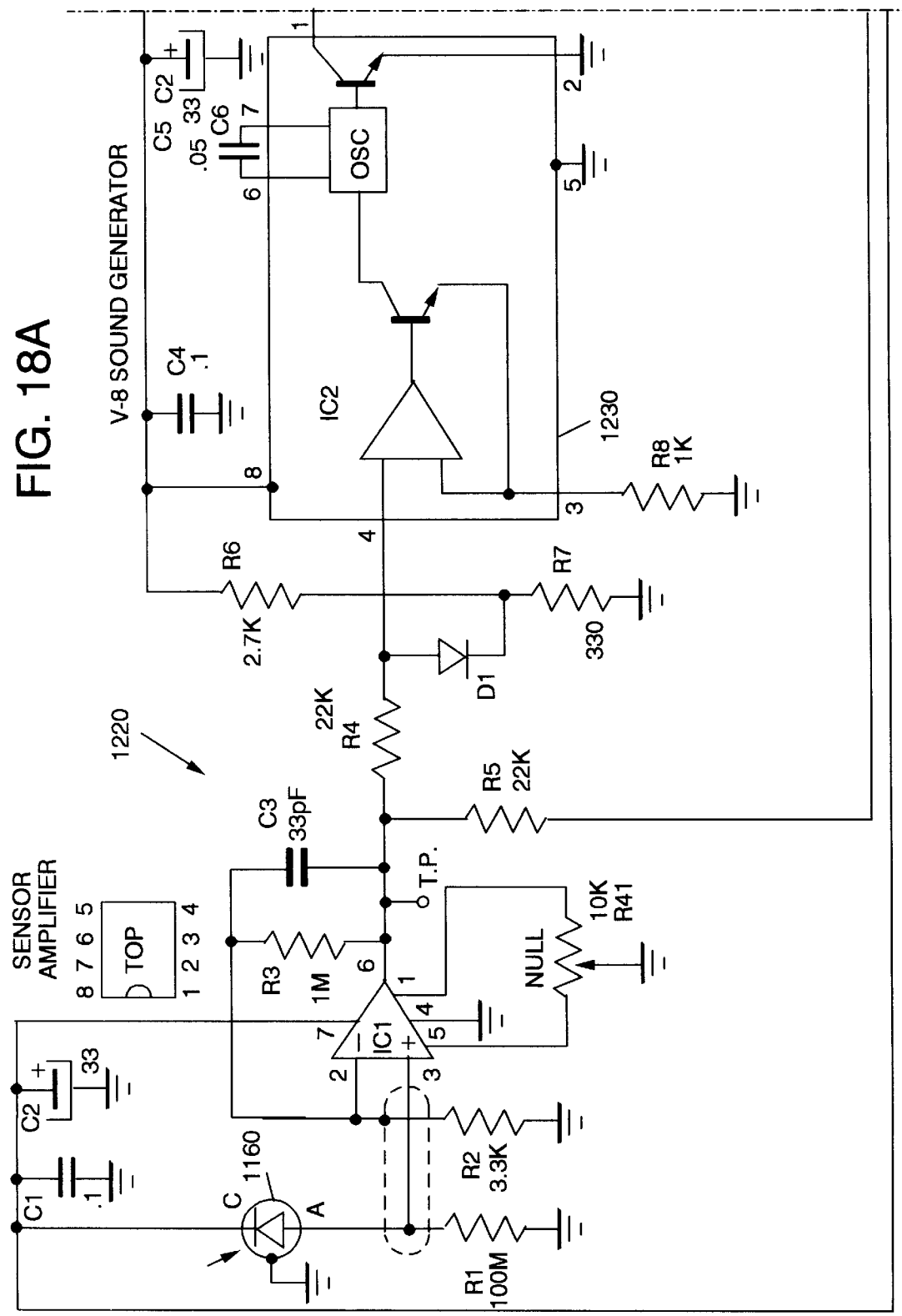
FIG. 18 is a detailed schematic of the tabletop instrument of FIGS. 16 and 17.
Figure 18B:
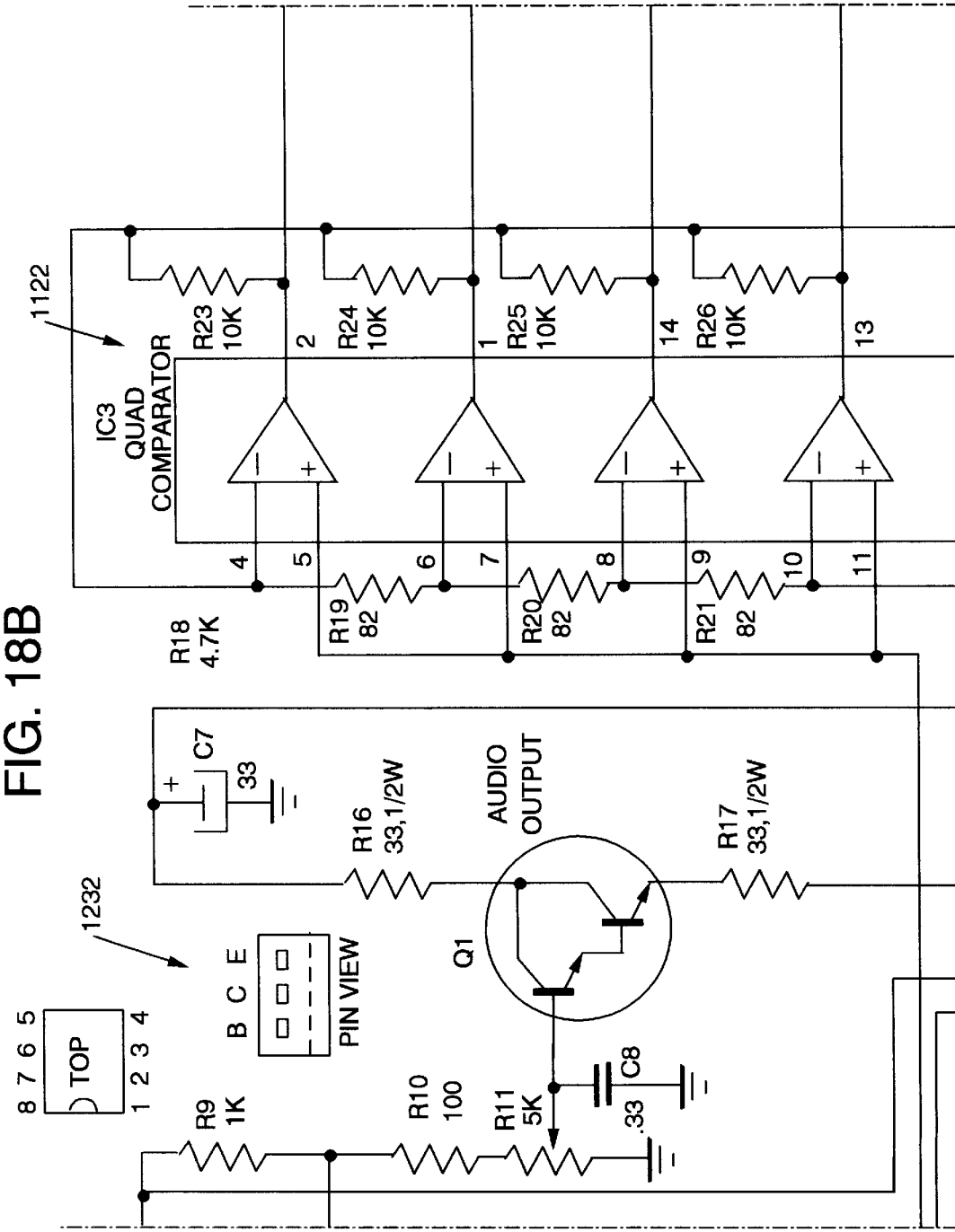
Figure 18C:
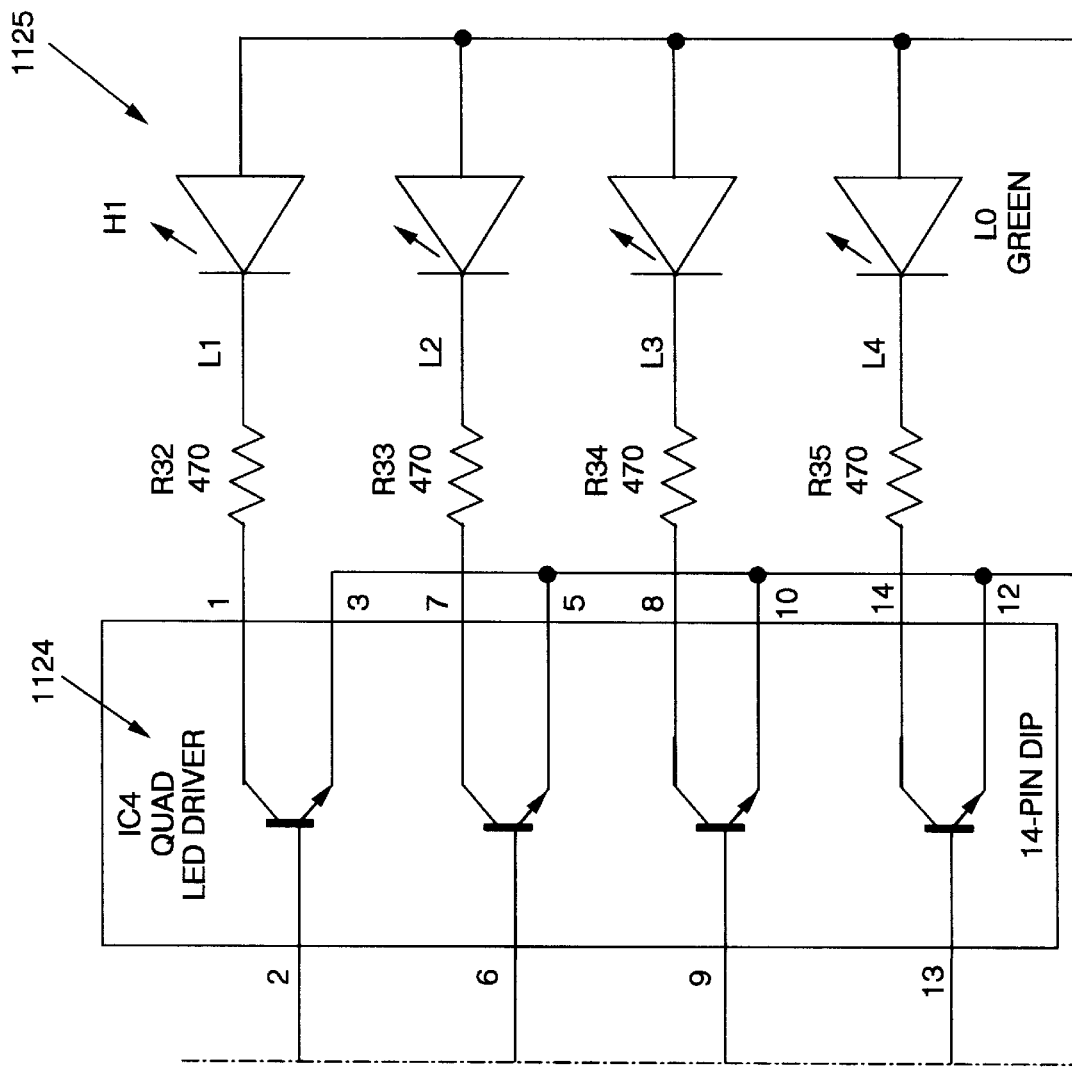
Figure 18D:
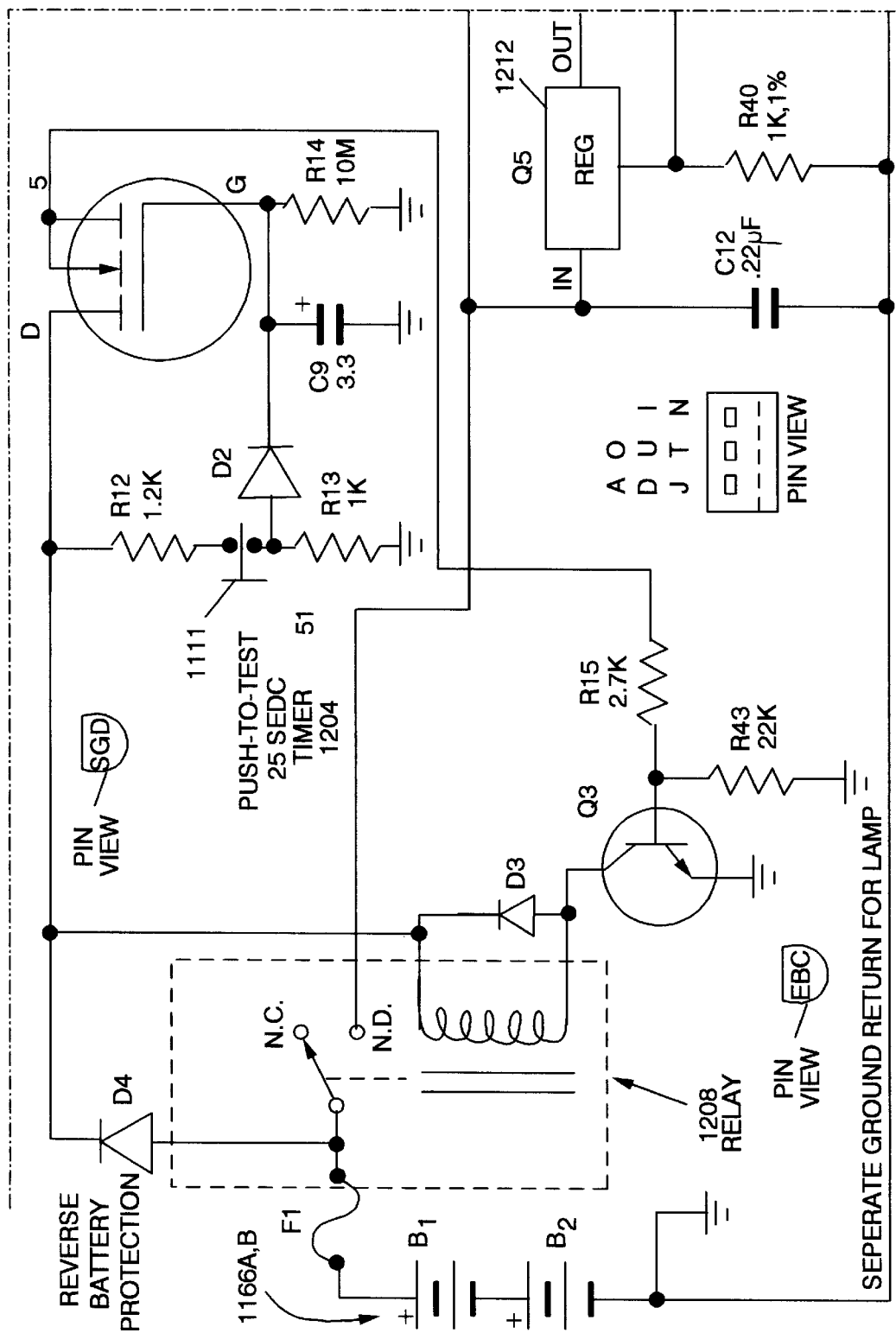
Figure 18E:
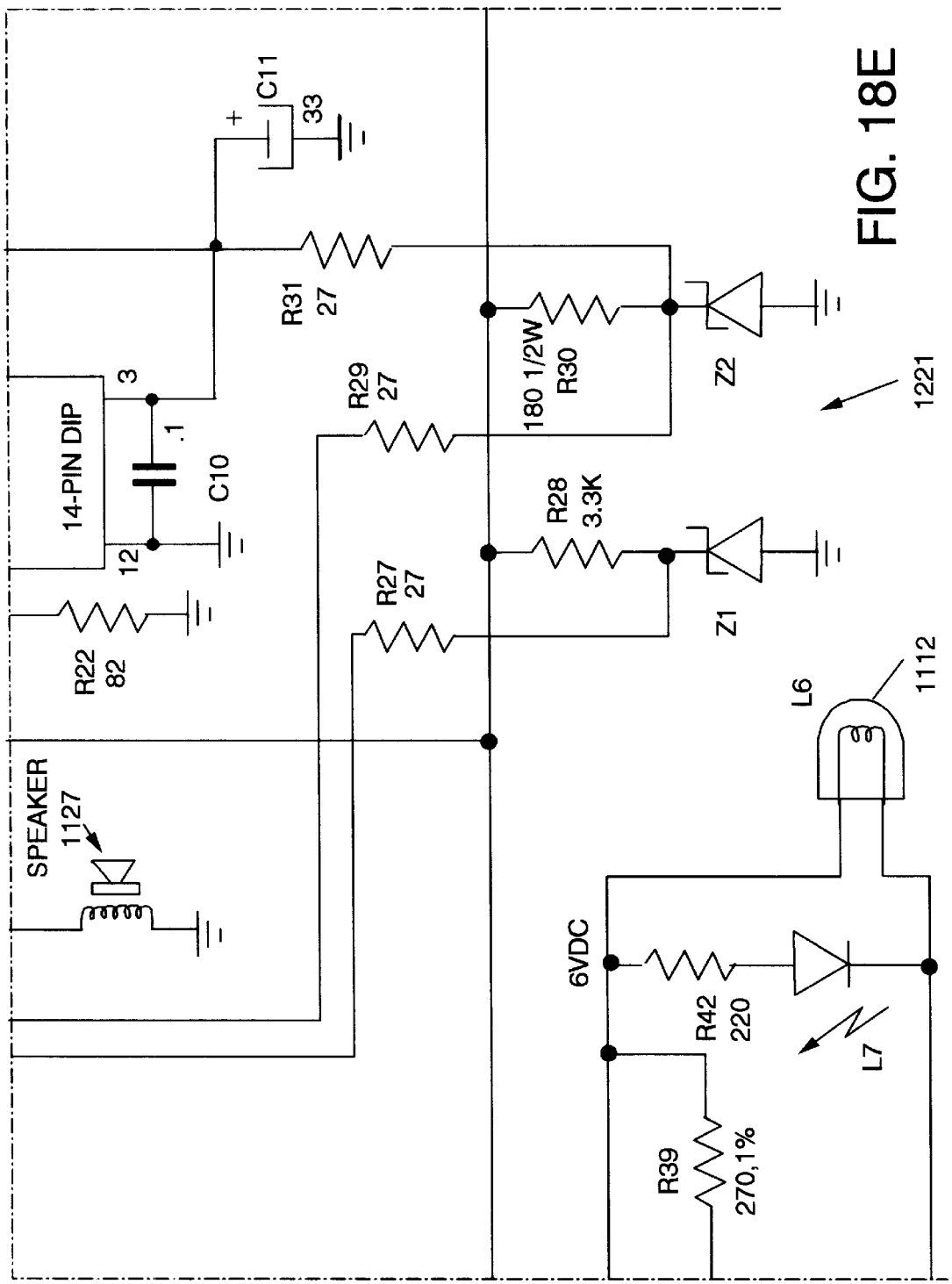

Normal operation of the instrument of FIG. 14 is as follows: All electronics and the light source 212 are turned on and allowed to stabilize. Computer 240 is initialized and starts the test process by reading the detector output of the first filter. All calibrations for the light source, filters and detectors are preinstalled in the computer program and the computer calculates the radiant flux intensity reaching the detector through the gemstone. The computer program, operating through a motor controller 250 selects the next filter in the series then takes another measurement. These steps are repeated for each filter. The information gathered preferably is presented in graph form with the radiant flux intensity plotted vs. the wavelength. These plots become signature characteristics of the particular gemstone material. The computer can make a comparison of the outputted graph with intensity versus wavelength plots from all other known gemstone types to correctly identify the subject gemstone. Two representative graphs are shown in FIGS. 15A and 15B. Graph 260 is a plot for a diamond, while graph 270 is a plot for a silicon carbide gemstone.

While the invention has been described in connection with certain illustrated embodiments, it will be appreciated that modifications may be made without departing from the true spirit and scope of the invention.

That which is claimed is:

1. A method of distinguishing between silicon carbide and diamond gemstones comprising determining whether a gemstone having the appearance of diamond transmits ultraviolet energy in an energy band lying within the range from about 310 nm to 400 nm and, therefore, is a diamond, or whether the gemstone absorbs ultraviolet energy in said band and is, therefore, silicon carbide, said method being carried out by the steps of:

irradiating a target gemstone that is either silicon carbide or diamond with ultraviolet energy in a band within the range of about 310 nm to 400 nm; while holding a flat surface of the target gemstone in physical contact with-the light receiving end of a light pipe; while sensing ultraviolet energy in said band emanating from an opposite light emitting end of the light pipe;

generating an output to the operator that is a function of the intensity of the ultraviolet energy in said band that is sensed;

moving the target gemstone flat surface and the light receiving end of the light pipe with respect to each other, while maintaining physical contact therebetween to assure satisfactory light transmission to the light pipe; and after moving the target gemstone flat surface with respect to the light receiving end of the light pipe, determining from the output whether the target gemstone transmitted ultraviolet energy within said band and, therefore, is a diamond, or whether the target gemstone absorbed ultraviolet energy in said band and is, therefore, silicon carbide.

2. The method of claim 1 including the step of utilizing a light pipe in the form of a fiber optic strand having a light receiving end with dimensions small enough to permit it to be placed completely on the target gemstone flat surface.

3. The method of claim 1 including the step of generating a variable output to the operator in the form of an audio output whose pitch increases in response to sensing increased levels of ultraviolet energy at the light emitting end of the light pipe.

4. The method of claim 1 including the step of generating a variable output to the operator in the form of a visual light emitting output that increases in intensity, size or number in response to sensing increased levels of ultraviolet energy at the light emitting end of the light pipe.

5. The method of claim 1 including the step of generating the output as both an audio output and a visual output.

6. The method of claim 1 wherein the target gemstone is a mounted gemstone having a flat table, and the step of holding a flat surface of the target gemstone in physical contact with the light receiving end of a light pipe comprises manually grasping the mount of the target gemstone and positioning the target gemstone so that the table thereof is held in physical contact with the light pipe.

7. The method of claim 1 wherein said step of sensing ultraviolet energy is carried out by locating a solid state photodetector in light-receiving relationship with respect to the light emitting end of the light pipe and at least roughly matching the size of the active area of the photodetector to the light output area of the light pipe.

8. The method of claim 1 wherein the step of irradiating the target gemstone is carried out by flooding the gemstone with ultraviolet light in said band, and wherein the light receiving end of the light pipe is held in physical contact with the table of the gemstone in order to receive light that has been internally reflected within the gemstone before emerging from the table.

9. An apparatus for use primarily by jewelers and appraisers to distinguish a silicon carbide gemstone from a diamond gemstone, said apparatus comprising:

a light source outputting ultraviolet energy in a band within a range of about 310 nm to 400 nm, said apparatus defining an area accessible to a user of the apparatus where a mounted or unmounted target gemstone that is either silicon carbide or diamond may be flooded by light from the light source;

a light pipe having a light receiving end and a light emitting end, said light receiving end being located in the mentioned area that is flooded by said light source where the table of a silicon carbide or diamond target gemstone may be held in place against the light receiving end, the light receiving end of said light pipe having dimensions small enough to permit it to be placed completely on the approximately 0.065 inch wide table of a round brilliant cut diamond or silicon carbide gemstone of about 0.1 carat;

a solid state photodetector located in light-receiving relationship with respect to the light emitting end of the light pipe, said photodetector having an active area with a size in the range from about 0.0005 cm$^2$ to about 0.05 cm$^2$ so as to at least roughly correspond to the light output area of the light pipe, and said photodetector having a responsivity to ultraviolet light in said band that is greater than about 2 mA/W to permit generation of a reliable, processable signal based upon the limited amount of light available through the light pipe when the target gemstone is diamond; and means coupled to said photodetector for producing an output to the operator of the apparatus to permit the operator to determine whether the target gemstone transmitted ultraviolet energy within said band and, therefore, is a diamond, or whether the target gemstone absorbed ultraviolet energy in said band and is, therefore, silicon carbide.

10. The apparatus of claim 9 wherein said photodetector is operable in a photoconductance mode wherein the conductance of the photodetector varies as a function of the intensity of ultraviolet light incident thereon.

11. The apparatus of claim 9 wherein said means for producing an output comprises an audio output circuit including a speaker whose pitch increases in response to increasing ultraviolet energy incident on the phtetector.

12. The apparatus of claim 9 wherein said means for producing an output comprises a visual output circuit including a visual display that indicates increasing ultraviolet energy incident on the photodetector.

13. The apparatus of claim 12 wherein said visual output circuit includes multiple LED's driven through a voltage level comparator.

14. The apparatus of claim 9 wherein said light pipe is a fiberoptic strand with a diameter in the range of about 0.030 inch to 0.060 inch.

15. The apparatus of claim 9 wherein said light pipe is a fiberoptic strand with a diameter on the order of 0.041 inch.

16. The apparatus of claim 9 wherein said photodetector has under short circuit current conditions, a responsivity to ultraviolet light in said band greater than about 10 mA/W.

17. The apparatus of claim 9 wherein said photodetector has under short circuit current conditions, a responsivity to ultraviolet light in said band on the order of about 20 mA/W.

18. The apparatus of claim 9 wherein said photodetector is a silicon carbide photodetector chip having, under short circuit current conditions, a responsivity to ultraviolet light in said band greater than about 10 mA/W and a dark current, under test condition V=$^-$1 V, lower than 1 picoamp.

19. The apparatus of claim 9 wherein said active layer semiconductor material is selected from the group consisting of silicon, gallium arsenide, silicon carbide, gallium nitride, aluminum nitride, zinc selenide, gallium nitride/aluminum nitride alloy, aluminum nitride/silicon carbide alloy and aluminum gallium nitride/gallium nitride heterojunction.

20. The apparatus of claim 9 wherein said light pipe comprises a fiberoptic strand.

21. The apparatus of claim 9 wherein said light source is an incandescent lamp.

22. An apparatus for use primarily by jewelers and appraisers to distinguish a silicon carbide gemstone from a diamond gemstone, said apparatus comprising:

a light source for flooding a target gemstone that is either silicon carbide or diamond with light containing ultraviolet energy in a band within the range of about 310 nm to 400 nm;

a solid state photodetector located in light-receiving relationship with respect to light from the light source that has traveled through a target gemstone, said photodetector including an active layer of semiconductor material having a responsivity of at least about 2 mA/W to ultraviolet energy in said band but no appreciable responsivity to energy above about 400 nm, and said photodetector further having a dark current, under test condition V=1V, lower than about 1 picoamp and the active layer semiconductor material of the photodetector being selected from the group consisting of silicon, gallium arsenide, silicon carbide, gallium nitride, aluminum nitride, zinc selenide, gallium nitride/aluminum nitride alloy, aluminum nitride/silicon carbide alloy and aluminum gallium nitride/gallium nitride heterojunction; and means coupled to said photodetector for producing an output to the operator of the apparatus to permit the operator to determine whether the target gemstone transmitted ultraviolet energy within said band and, therefore, is a diamond, or whether the target gemstone absorbed ultraviolet energy in said band and is, therefore, silicon carbide.

23. The apparatus of claim 22 wherein said light, source is an incandescent lamp.

24. The apparatus of claim 22 wherein said light source is a light emitting semiconductor.

25. The apparatus of claim 22 wherein said light source is a pn junction gallium nitride light emitting diode.

26. The apparatus of claim 22 wherein the semiconductor material of the active layer is silicon carbide with an active layer size in the range from about 0.0005 cm$^2$ to about 0.05 cm$^2$ and a responsivity to ultraviolet light in said band greater than about 10 mA/W.

27. The apparatus of claim 26 wherein the silicon carbide photodetector has a dark current, under test condition V=−1V, lower than about 1 fentoamp.

28. The apparatus of claim 26 including a fiber optic strand for carrying light from the table of a target gemstone to the photodetector, said strand having cross-sectional dimensions permitting a light receiving end thereof to be placed completely on the table of a 0.1 carat round brilliant cut gemstone.

* * * * *